US012638461B2

(12) United States Patent
Samproni

(10) Patent No.: US 12,638,461 B2
(45) Date of Patent: May 26, 2026

(54) DEVICE AND METHOD TO EVALUATE A FLUID SAMPLE ON A SINGLE-USE MULTIANALYTE CONSUMABLE

(71) Applicant: Siemens Healthcare Diagnostics Inc., Tarrytown, NY (US)

(72) Inventor: Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1096 days.

(21) Appl. No.: 17/636,075

(22) PCT Filed: Aug. 27, 2020

(86) PCT No.: PCT/US2020/048105
§ 371 (c)(1),
(2) Date: Feb. 17, 2022

(87) PCT Pub. No.: WO2021/041607
PCT Pub. Date: Mar. 4, 2021

(65) Prior Publication Data
US 2022/0357347 A1      Nov. 10, 2022

Related U.S. Application Data

(60) Provisional application No. 62/893,357, filed on Aug. 29, 2019.

(51) Int. Cl.
*G01N 33/72* (2006.01)
*B01L 3/00* (2006.01)
(Continued)

(52) U.S. Cl.
CPC ...... *G01N 33/721* (2013.01); *B01L 3/502753* (2013.01); *G01N 21/251* (2013.01);
(Continued)

(58) Field of Classification Search
None
See application file for complete search history.

(56) References Cited

U.S. PATENT DOCUMENTS

| | | |
|---|---|---|
| 4,631,130 A | 12/1986 | Watanabe |
| 9,157,903 B2 | 10/2015 | Seifried et al. |
| | (Continued) | |

FOREIGN PATENT DOCUMENTS

| | | |
|---|---|---|
| CA | 2020029 A1 | 1/1991 |
| EP | 3890871 A1 | 10/2021 |
| | (Continued) | |

OTHER PUBLICATIONS

International Search Report and Written Opinion of International Application No. PCT/US2020/048105 dated Nov. 20, 2020.

*Primary Examiner* — Lore R Jarrett

(57) ABSTRACT

Single-use diagnostic consumables for use in performing multiple analyses on a fluid sample are provided. The diagnostic consumables include a first sensing region configured for analysis of at least one analyte in a fluid sample that has been received by the diagnostic consumable. The diagnostic consumable further includes a fluid transport material configured to flow a portion of the fluid sample into a second sensing region fluidically connected to the fluid transport material and configured for performing a second analysis of the fluid sample. Methods for performing multiple analyses of a fluid sample on a single-use diagnostic consumable are also provided.

25 Claims, 10 Drawing Sheets

(51) Int. Cl.
  G01N 21/25 (2006.01)
  G01N 21/84 (2006.01)
  G01N 35/00 (2006.01)
(52) U.S. Cl.
  CPC ....... G01N 21/8483 (2013.01); G01N 33/726
      (2013.01); G01N 35/00029 (2013.01); *B01L*
      *2200/10* (2013.01); *B01L 2200/16* (2013.01);
        *B01L 2300/021* (2013.01); *B01L 2300/0636*
          (2013.01); *B01L 2300/0681* (2013.01)

(56) References Cited

U.S. PATENT DOCUMENTS

| | | | |
|---|---|---|---|
| 2013/0164779 | A1 | 6/2013 | Kelley et al. |
| 2017/0108516 | A1 | 4/2017 | Ledden et al. |
| 2019/0041407 | A1 | 2/2019 | Yang et al. |

FOREIGN PATENT DOCUMENTS

| | | | |
|---|---|---|---|
| JP | 2007024898 | A | 2/2007 |
| JP | 2008020287 | A | 1/2008 |
| JP | 2008516261 | A | 5/2008 |
| JP | 2010078608 | A | 4/2010 |
| JP | 2011058956 | A | 3/2011 |
| JP | 2011508872 | A | 3/2011 |
| JP | 2014002143 | A | 9/2014 |
| JP | 2017508971 | A | 3/2017 |
| JP | 2019113425 | A | 7/2019 |
| JP | 2020502478 | A | 1/2020 |
| JP | 2021508052 | A | 2/2021 |
| WO | 2004074846 | A1 | 9/2004 |
| WO | 2013096804 | A2 | 6/2013 |
| WO | 2020118021 | A1 | 6/2020 |

DEVICE AND METHOD TO EVALUATE A FLUID SAMPLE ON A SINGLE-USE MULTIANALYTE CONSUMABLE

CROSS REFERENCE TO RELATED APPLICATIONS

This disclosure is a 371 of PCT/US2020/048105, filed Aug. 27, 2020, which claims priority under 35 U.S.C. § 119 (e) to U.S. Provisional Patent Application No. 62/893,357, filed Aug. 29, 2019. The entire contents of the above-referenced patent applications are hereby expressly incorporated herein by reference in their entireties for all purposes.

FIELD

This disclosure relates generally to fluidic devices, and in particular to fluid sample analysis on single-use diagnostic consumables.

BACKGROUND

Fluidic devices are used to control and/or manipulate fluids for any of a variety of applications. A fluidic device typically includes one or more channels that constrain the flow of a fluid in the device. Fluidic diagnostic devices typically incorporate and/or are coupled to one or more sensors to provide sensing capabilities. For example, a sample fluid could be pumped through channels in a fluidic device to a sensing region of the fluidic device in order to be exposed to a sensor. The sensor could be incorporated into the fluidic device and/or part of a separate device to which the sensing region is exposed in order to measure one or more properties of the fluid. In the context of medical diagnostic devices, fluidic devices have been used in the measurement of one or more properties of a bodily fluid. By way of example, a blood sample could be added to a fluidic device to control and/or manipulate the blood sample in order to measure the concentration of certain analytes in the blood.

In recent years, fluidic devices have attracted attention for use in the field as diagnostic devices for point-of-care testing. Point-of-care testing refers generally to medical testing at or near the site of patient care, such as in an emergency room. A desired outcome of such tests is often rapid and accurate lab results to determine a next course of action in the patient care. A number of such point-of-care tests involve perform one or more assays of a blood sample from the patient. For the purposes of the instant disclosure, an assay may be defined as a procedure for quantifying the amount or the functional activity of an analyte in a liquid sample. An assay may involve a variety of operations on the fluidic device, such as sample introduction, preparation, metering, sample/reagent mixing, liquid transport, and detection, etc.

Typical diagnostic assays involve manipulating small volumes of fluid with precise control, which can be challenging due to several factors, such as fluid loss in transport, capillary effects, impact of gravity, trapped air and others. Additionally, several assay processes such as mixing and incubation can also pose unique challenges in miniature fluidic devices. For disposable fluidic devices used as diagnostic consumables, these challenges are often compounded by the need for a solution that is both cost-effective and provides the level of precision needed to deliver the required assay performance. Improving the efficiency, reliability and repeatability of measurements is an important consideration in the design of diagnostic devices, and particularly in the context of single-use diagnostic consumables.

SUMMARY

According to a first aspect, the present disclosure provides a single-use diagnostic consumable for use in performing multiple analyses of fluid sample. The diagnostic consumable includes a first sensing region that includes at least one sensor configured for analysis of at least one analyte in a fluid sample that has been received by the diagnostic consumable. The diagnostic consumable further includes a second sensing region configured for a second analysis of the fluid sample, and a fluid transport material configured to flow a portion of the fluid sample into the second sensing region.

In some embodiments, the second sensing region is adjacent to one end of the fluid transport material.

In some embodiments, the fluid transport material defines a path for capillary fluid flow through the fluid transport material to the second sensing region.

In some embodiments, at least a portion of the second sensing region is optically transparent to permit an optical assay of the portion of the fluid sample within the second sensing region.

In some embodiments, the second sensing region is configured for colorimetric analysis.

In some embodiments, the fluid transport material comprises at least one component configured to selectively bind to an analyte of interest in the fluid sample.

In some embodiments, the fluid sample comprises a bodily fluid sample, such as blood or urine.

In some embodiments, the bodily fluid sample is a whole blood sample and the fluid transport material acts as a plasma separation membrane to separate plasma and blood cells in the whole blood sample to produce a plasma sample for analysis in the second sensing region.

In some embodiments, the fluid sample is a whole blood sample and the at least one component configured to selectively bind to an analyte of interest in the fluid sample includes a least one type of red blood cell binding or agglutination material.

In some embodiments, the fluid sample is a whole blood sample and the fluid transport material is configured as a chromatographic detection pad for detecting a presence of free hemoglobin in the whole blood sample.

In some embodiments, the first sensing region includes a sensor array for analysis of multiple analytes in the fluid sample.

In some embodiments, the sensor array includes electrochemical sensors configured for measuring concentrations of gases, electrolytes and/or metabolites in the fluid sample.

In some embodiments, the diagnostic consumable further comprises a sample input port for receiving the fluid sample, the sample input port being fluidically connected to the first sensing region and the fluid transport material.

In some embodiments, the fluid transport material is fluidically connected downstream of the first sensing region relative to the sample input port.

In some embodiments, the fluid transport material is fluidically connected upstream of the first sensing region relative to the sample input port.

In some embodiments, the fluid transport material substantially surrounds the sample input port.

In some embodiments, the fluid transport material has a first end adjacent to the sample input port and a second end adjacent to the second sensing region.

In some embodiments, the diagnostic consumable includes one or more sample distribution channels fluidically connected to the sample input port, the first sensing region and the fluid transport material.

In some embodiments, the one or more sample distribution channels direct a first portion of the fluid sample to the first sensing region for analysis of the fluid sample, and direct a second portion of the fluid sample into fluidic contact with the fluid transport material.

In some embodiments, the single-use diagnostic consumable further includes a third sensing region, fluidically connected to the sample input port, and configured for analysis of at least one analyte in the fluid sample. In such embodiments, the analysis in the third sensing region differs from the analysis in the first sensing region.

In some embodiments, the third sensing region includes a channel fluidically connected to the sample input port. The channel may have disposed thereon a material for mixing with the fluid sample to generate a prepared fluid sample by flowing a portion of the fluid sample through the channel. In such embodiments, the single-use diagnostic consumable may further include a chamber, fluidically connected to the channel, and configured for containing at least a portion of the prepared fluid sample for analysis.

In some embodiments, at least a portion of the chamber is optically transparent to permit an optical assay of the prepared fluid sample.

In some embodiments, the fluid sample comprises a whole blood sample and the channel fluidically connected to the sample input port is configured as a hemolysis channel having disposed thereon a haemolytic reagent for hemolyzing a portion of the fluid sample to generate a hemolyzed blood sample.

According to a second aspect, the present disclosure provides a method for performing multiple analyses of a fluid sample on a single-use diagnostic consumable. The method includes receiving a fluid sample on the single-use diagnostic consumable and analyzing the fluid sample in a first sensing region of the diagnostic consumable using at least one sensor within the first sensing region. The method further includes flowing a portion of the fluid sample into a second sensing region of the diagnostic consumable using a fluid transport material on the diagnostic consumable, and analyzing the portion of the fluid sample in the second sensing region of the diagnostic consumable. In some embodiments, the analysis of the portion of the fluid sample in the second sensing region is an optical analysis. In such embodiments, at least a portion of the second sensing region may be optically transparent to permit an optical assay of the portion of the fluid sample within the second sensing region.

In some embodiments of the method, the fluid sample comprises a whole blood sample. In such embodiments, flowing a portion of the fluid sample into the second sensing region may include separating plasma and blood cells in the whole blood sample using the fluid transport material to produce a plasma sample that may be optically analyzed in the second sensing region. For example, optically analyzing the plasma sample could include performing a colorimetric analysis of the plasma sample. In some such embodiments, performing a colorimetric analysis of the plasma sample may include measuring an amount of red light that is reflected by the plasma sample in the second sensing region, and determining a level of free hemoglobin in the whole blood sample based on the measured amount of reflected red light.

In some embodiments of the method, the fluid transport material may include at least one component configured to selectively bind to an analyte of interest in the fluid sample. In some such embodiments, optically analyzing the portion of the fluid sample in the second sensing region may include optically detecting whether a bound analyte of interest is present in the fluid sample.

In some embodiments of the method, analyzing the fluid sample in the first sensing region using at least one sensor in the first sensing region may involve analyzing multiple analytes in the fluid sample using a sensor array in the first sensing region.

In some embodiments of the method, analyzing multiple analytes in the fluid sample using a sensor array in the first sensing region may involve measuring concentrations of gases, electrolytes and/or metabolites in the fluid sample using an array of electrochemical sensors in the first sensing region.

In some embodiments of the method, the diagnostic consumable includes a sample input port for receiving the fluid sample and the method further includes directing a first portion of the fluid sample from the sample input port to the first sensing region for analysis of the fluid sample, and directing a second portion of the fluid sample from the sample input port into fluidic contact with the fluid transport material.

In some embodiments of the method, the fluid sample comprises a whole blood sample and the method further includes hemolyzing a portion of the whole blood sample on the diagnostic consumable to generate a hemolyzed blood sample, and optically analyzing the hemolyzed blood sample in a third sensing region on the diagnostic consumable, at least a portion of the third sensing region being optically transparent to permit an optical assay of the hemolyzed blood sample.

Other aspects and features of embodiments of the present disclosure will become apparent to those ordinarily skilled in the art upon review of the following description.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION

Figure 1A:
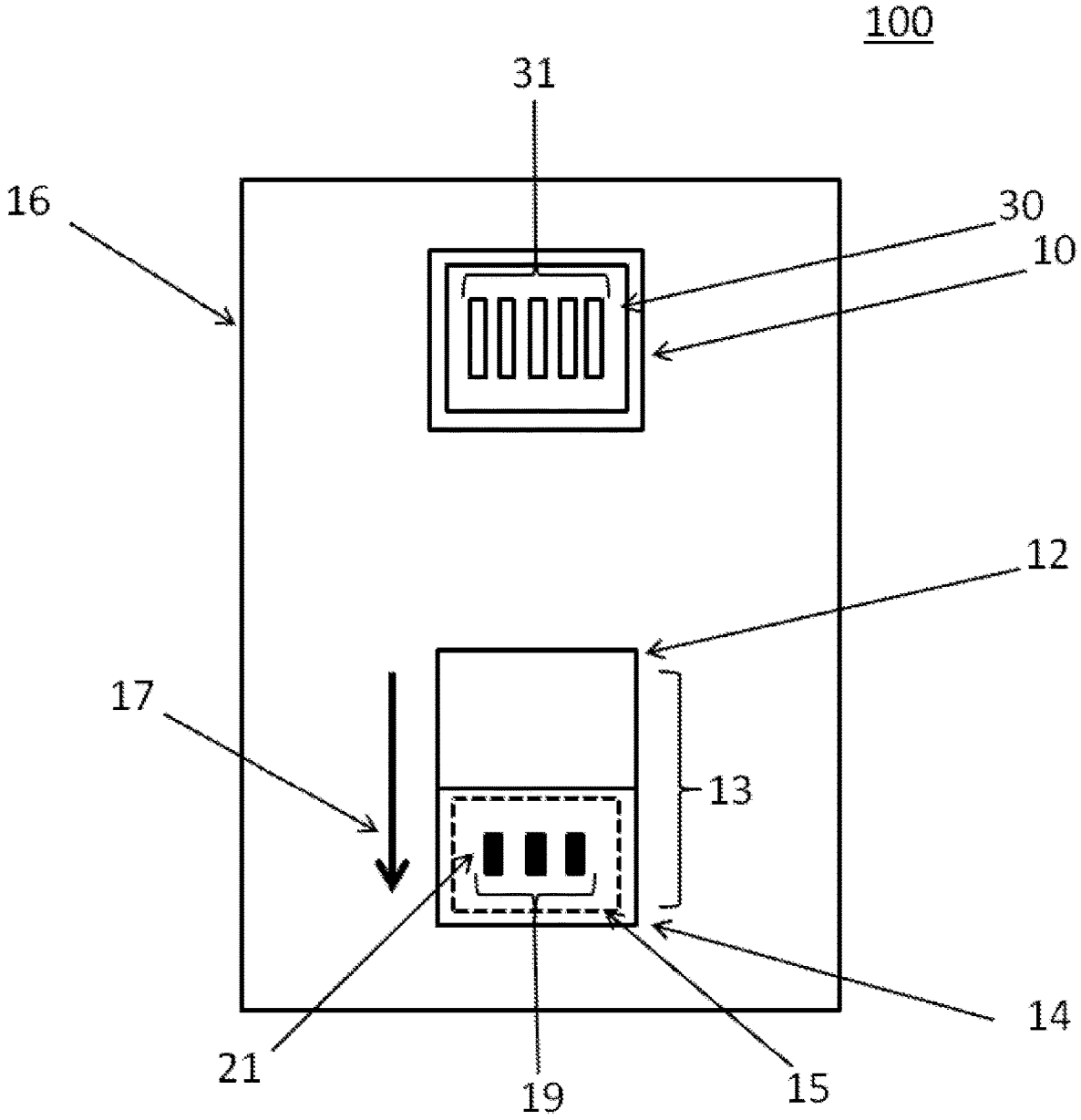
FIG. 1A is a plan view of a first example of a diagnostic consumable for use in the analysis of whole blood and plasma constructed in accordance with an embodiment of the present disclosure.

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, may be analog and/or digital, components, or one or more suitably programmed microprocessors and associated hardware and software, or hardwired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transitory memory. Exemplary non-transitory memory includes random access memory, read only memory, flash memory or the like. Such non-transitory memory may be electrically based or optically based.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement.

In accordance with one aspect, there are provided devices and methods for performing multiple analyses of a fluid sample on a single-use diagnostic consumable. More specifically, devices and methods are disclosed herein in which a first analysis of a fluid sample that has been introduced onto a single-use diagnostic consumable is performed in a first sensing region of the single-use diagnostic consumable, and a fluid transport material on the single-use diagnostic consumable flows a portion of the fluid sample into a second sensing region that is configured for a second analysis of the portion of the fluid sample within the second sensing region. The fluid transport material may be implemented using a wicking material such as porous/permeable polymers, gels (e.g. acrylamide or agarose), glass fibers, cellulose fibers/paper and the like. In some embodiments, the fluid sample may be a bodily fluid, such as blood or urine. For example, in some embodiments the fluid sample may be a whole blood sample and the fluid transport material may be configured to separate plasma from red blood cells to produce a plasma sample for analysis in the second sensing region of the single-use diagnostic consumable. Advantageously, such embodiments permit a plasma sample to be separated from a portion of a whole blood sample on a single-use diagnostic consumable so that both the whole blood sample and the plasma sample can be analyzed on the single-use diagnostic consumable. To perform such analyses, the diagnostic consumable could be inserted into a diagnostic instrument such as a diagnostic consumable reader module. The blood sample may have been collected from an animal, such as a human, or a non-human (such as a cat, dog, cow, horse, fish, or the like). Depending on the implementation, a blood sample may be introduced into the diagnostic consumable either before or after the diagnostic consumable is inserted into the diagnostic instrument. The diagnostic instrument could then use and/or control the diagnostic consumable to perform one or more assays on the blood sample and the plasma sample that has been separated from the blood sample on the diagnostic consumable. In some embodiments, an analysis of the plasma sample on the diagnostic consumable may be done visually using the human eye and/or using an optical reader that is part of the diagnostic instrument. The combination of the diagnostic consumable and the diagnostic instrument could be considered a blood analysis system.

The capability to separate and analyze whole blood and plasma on a single-use diagnostic consumable potentially improves workflow and enables visual/machine-readable evaluation of blood components (i.e. hemolysis, icterus, lipemia). For example, separating plasma and blood cells in a whole blood sample to produce a plasma sample on a single-use diagnostic consumable could improve workflow by eliminating the need to separately centrifuge blood to separate the plasma. Furthermore, as discussed in further detail below, a separate dosing step for addition of binding chemicals could also potentially be eliminated, because the binding chemicals may be included on the diagnostic consumable and exposed to the whole blood sample during the plasma separation process on the diagnostic consumable.

Although many of the example embodiments described below relate to single-use diagnostic consumables configured for the evaluation of plasma and whole blood, embodiments of the present disclosure are not limited to blood analysis and could also or instead relate to other types of fluid sample analyses in diagnostic consumables or other types of analysis systems. For example, a single-use diagnostic consumable in accordance with the present disclosure may include fluid transport material configured for use as a lateral flow immunoassay to confirm the presence or absence of a target analyte in a fluid sample, such as pathogens or biomarkers in humans or animals, or contaminants in water supplies, foodstuffs, or animal feeds, while one or more additional analyses are carried out on the fluid sample using one or more sensors in other sensing regions on the diagnostic consumable.

Referring now to the Figures and in particular to FIG. 1A, shown therein is a plan view of a diagnostic consumable 100 for use in the analysis of whole blood and plasma constructed in accordance with an embodiment of the present disclosure. In general, the diagnostic consumable 100 includes a first sensing region 10, a second sensing region 14, and fluid transport material 12, which in this embodiment is configured as a plasma separation membrane 12.

The first sensing region 10 is configured for analysis of one or more analytes in a whole blood sample (not shown) that has been introduced onto the diagnostic consumable 100. The first sensing region 10 may include one or more sensors for measuring the concentration of certain analytes in the blood sample. For example, the first sensing region 10 may include a sensor array 30 that includes multiple sensors 31. The sensors 31 could be coupled to electrode elements (not shown) for forming an electrical connection to a measuring circuit in a diagnostic instrument, for example. In use, the sensors 31 could be used to measure one or more properties of a blood sample in the first sensing region 10. The sensors 31 could be electrochemical sensors that are used for measuring concentrations of gases, electrolytes and/or metabolites. The sensors 31 could include potentiometric sensors to measure sodium, potassium, ionized calcium, chloride, urea, $TCO_2$, pH levels and/or $CO_2$ partial pressure; amperometric sensors to measure $O_2$ partial pressure, glucose, creatinine, and/or lactate; and/or conductometric sensors to measure hematocrit, for example. Sensors and sensor arrays with many different electrode/sensor numbers and geometries are possible. The number and geometry of the sensors 31 shown in FIG. 1A is provided by way of example only.

The plasma separation membrane 12 is configured to separate plasma and blood cells in the whole blood sample to generate a plasma sample. In some embodiments, the plasma separation membrane 12 may be made of a material that has pores through which the blood sample moves by capillary action (which may also be referred to as capillary flow), which causes the separation of undamaged blood cells and plasma in the blood sample as described more fully in U.S. patent application Ser. No. 15/317,748, the entirety of which is incorporated herein by reference. In such embodiments, the plasma separation membrane 12 may be made of any material through which the whole blood sample may flow by capillary action. As an example, the plasma separation membrane 12 may be a nitrocellulose membrane. The majority of the pores of the plasma separation membrane 12 may all be substantially the same size or fall within a range of values selected to permit plasma to flow therethrough while substantially blocking/filtering the passage of undamaged blood cells. In other embodiments, in addition or instead of capillary action, the whole blood sample may be flowed through the plasma separation membrane by applying positive pressure to the blood sample upstream of the plasma separation membrane 12 to "push" the blood sample through the plasma separation membrane 12 and/or by applying negative pressure (i.e., vacuum pressure) downstream of the plasma separation membrane 12 to "pull" the blood sample through the plasma separation membrane 12. The second sensing region 14 can be considered to be downstream of the plasma separation membrane 12 in that the blood sample flows through the plasma separation membrane 12 via capillary action towards the second sensing region 14 in the direction of arrow 17.

The second sensing region 14 is fluidically connected to the plasma separation membrane 12 and is configured for analysis of the plasma sample that has passed through the plasma separation membrane. The second sensing region 14 may include a portion of the plasma separation membrane 12. For example, the plasma separation membrane 12 may be implemented as a chromatographic detection pad 13 (which may also be referred to as a lateral flow strip). For example, in some embodiments the chromatographic detection pad 13 may be used for the detection of hemolysis in the blood sample in order to inform a medical professional when the sample is compromised and may yield inaccurate test results. In such embodiments, the second sensing region 14 may include a downstream portion of the chromatographic detection pad 13. In other embodiments, the second sensing region 14 may include chamber or vessel for collecting the plasma sample after it has flowed through the plasma separation membrane 12. In such embodiments, a positive pressure upstream of the plasma separation membrane 12 and/or a negative pressure downstream of the plasma separation membrane 12 may be needed to flow the plasma through the plasma separation membrane 12 and into the second sensing region 14, because the capillarity of the plasma separation membrane 12 may otherwise retain a substantial portion of the plasma within the plasma separation membrane 12 and prevent it from flowing into the second sensing region 14. At least a portion 15 of the second sensing region 14 may be optically transparent to permit an optical assay of the plasma sample within the second sensing region 14. For example, the plasma in the second sensing region 14 may be analyzed by eye (colorimetrically) or analyzed by machine using an optical reader, such as a spectrophotometer or camera, having a field of view overlapping with the diagnostic consumable 100 such that the plasma within the second sensing region 14 is visible to the optical reader. For example, a degree of hemolysis could be determined based upon a colorimetric analysis of the plasma sample in the second sensing region 14. That is, when the plasma sample is devoid of hemolysis and is illuminated with white light, the plasma may be substantially devoid of any color, i.e., the sample will be transparent. When hemolysis has occurred within the sample, the plasma may be pink when the plasma is illuminated with white light. By correlating the color of the plasma with predetermined colors indicative of an extent of hemolysis occurring within other samples, the extent of hemolysis within the sample can be determined. Depending upon a color of a backdrop of the second sensing region 14, and/or color of illumination of the plasma, colors indicative of an extent of hemolysis may differ. Information indicative of an extent of hemolysis within the plasma sample can be used to determine whether the blood sample has hemolysis.

When severe enough, hemolysis may result in inaccurate blood analysis results. For example, in blood gas and electrolyte testing it is known that hemolysis will cause an increase in the sample potassium level. In addition, it is known that cardiac troponin T (cTnT) levels are decreased in samples with hemolysis and cardiac troponin I (cTnI) levels have been shown to be increased in samples with hemolysis. In embodiments in which a degree of hemolysis within the sample of blood is determined based on an analysis of the plasma sample in the second sensing region 14, the result may be used to decide whether or not one or more of the assays of the blood sample in the first sensing region 10 may be invalid and/or to adjust or "calibrate" the results of one or more of the assays of the blood sample in the first sensing region 10 to account for the degree of hemolysis.

As will be explained further below, the plasma separation membrane 12 may be treated with one or more binding chemicals to facilitate plasma separation and/or to act as markers for detection of one or more analytes in the plasma sample. For example, the plasma separation membrane 12 may be treated with a red blood cell (RBC) binding or agglutination material and/or one or more reagents or other binding chemicals that reacts with and/or binds to certain analytes of interest in the blood sample. For example, such reagents could include reagents that react to free hemoglobin present in the blood sample in order to permit detection of hemolysis in the blood sample. An exemplary reagent present in the plasma separation membrane 12 may accentuate the color change attributable to free hemoglobin in the second sensing region 14. Exemplary reagents of this type may utilize the peroxidase-like activity of hemoglobin, which catalyzes the reaction of diisopropylbenzene dihydroperoxide and 3,3',5,5'-tetramethylbenzidine. The resulting color ranges from orange through green and possibly up to blue. Alternatively, or instead, exemplary reagents could include reagents that react with other analytes of interest, such as a drug of abuse, such as barbituates, cannabinoids, cocaine metabolite, ethanol, ecstasy, methadone, methamphetamine and opiates. Exemplary reagents or binding chemicals may be located in the plasma separation membrane 12 and/or in the second sensing region 14. For example, exemplary reagents or binding chemicals 19 may be arranged into a strip 21 arranged perpendicular to the direction of flow (which is denoted by arrow 17) in the second sensing region 14.

The diagnostic consumable 100 may be implemented on a substrate 16. Exemplary materials that can be used to form the substrate 16 include fluid impermeable material(s) such as plastics, ceramics, glass, crystal, and the like. In an exemplary embodiment, the substrate 16 may be a plastic substrate obtained via a plastic injection molding process.

Figure 1B:
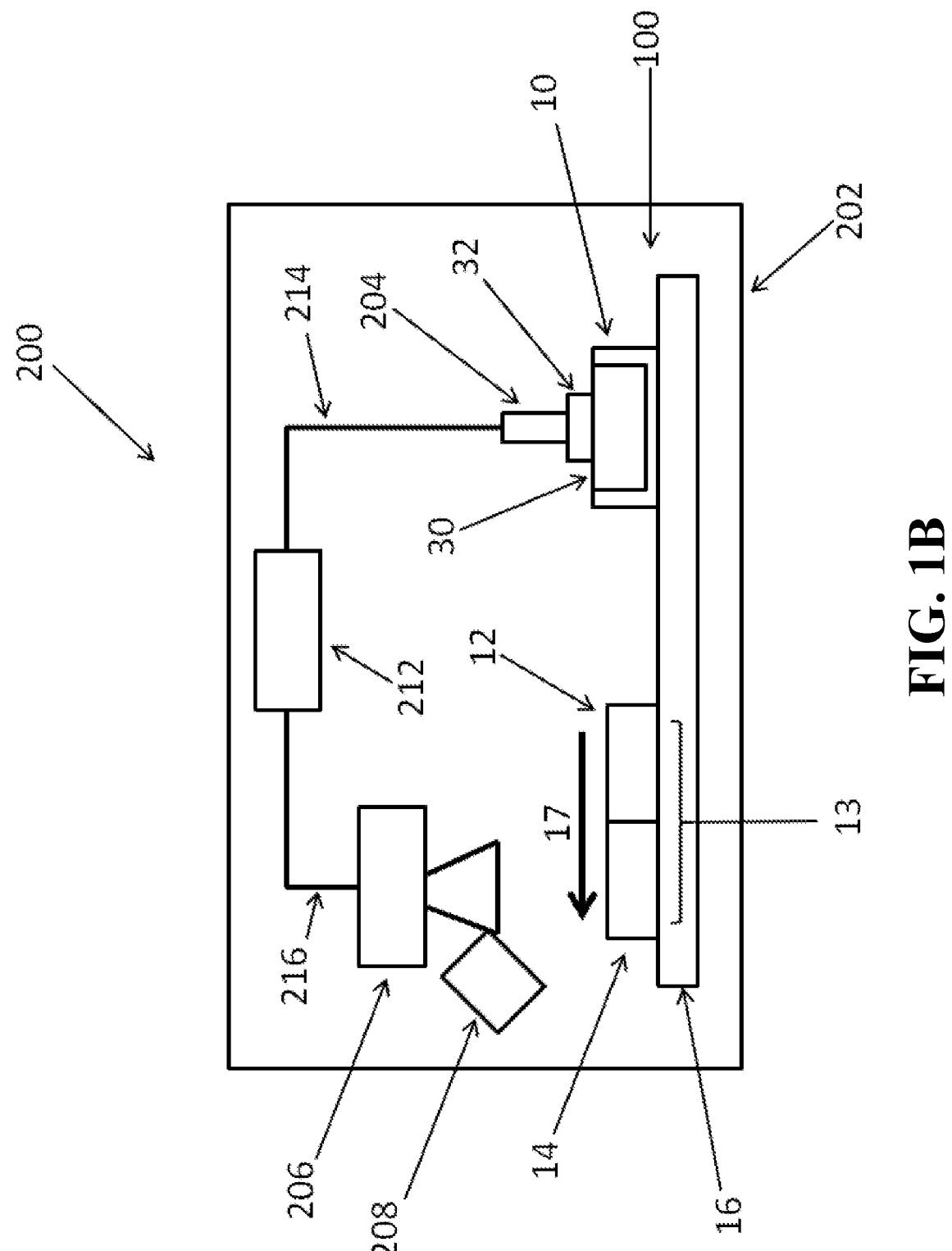
FIG. 1B illustrates an embodiment of a medical diagnostics instrument constructed in accordance with an embodiment of the present disclosure.

Referring now to FIG. 1B, shown therein is an embodiment of a medical diagnostics instrument 200 that may be used with the diagnostic consumable 100. Diagnostics instrument 200 comprises electrical contacts 204, an optical reader 206, a light source 208 directed at the second sensing region 14 of the diagnostic consumable 100, and a control unit 212. The optical reader 206 may be a spectrophotometer or camera as described above. The electrical contacts 204 may be provided with a shape that allows them to make electrical contact with electrodes 32 of the sensor array 30 in the first sensing region of the diagnostic consumable 100.

The diagnostics instrument 200 may be portable and have a housing 202 that includes a slot (not shown) sized and dimensioned to receive the diagnostic consumable 100 such that the second sensing region 14 is in the field of view of the optical reader 206 and the electrodes 32 of the sensor array 30 in the first sensing region 10 can be electrically contacted by the electrical contacts 204 of the diagnostic instrument 200. The housing 202 can be provided in a variety of shapes such as in a shape of a credit card reader, for instance.

The optical reader 206 captures an image of the plasma and any backdrop in the second sensing region 14 and sends the image to the control unit 212 in detection signals 216. The control unit 212 then analyzes the characteristics of the light reflected by the second sensing region 14 of the diagnostic consumable 100 based on the received image(s). As described above, in some embodiments the characteristics, such as the observable colors (e.g., red, orange, green, and blue), of the light reflected by the second sensing region 14 may be attributable to the presence of free hemoglobin or some other analyte of interest in the blood sample. Thus, the characteristics of the reflect light can be used by the processor to detect and/or quantify some characteristic of the analyte, such as an amount of free hemoglobin present in the blood sample. For example, the amount/intensity of red light reflected by the second sensing region 14 may be used to quantify the amount of free hemoglobin present in the blood sample. When the second sensing region 14 contains a reagent(s) that reacts with free hemoglobin, the amount/intensity of one or more of red, orange, green, or blue light reflected by the second sensing region 14 can be used to quantify the amount of free hemoglobin present in the blood sample. Thus, in such embodiments, the control unit 212 may be able to determine the amount of free hemoglobin in the blood sample by, for example, comparing the measured amounts of the observable colors of the light reflected by the second sensing region 14 against known reference values.

In an embodiment, the light source 208 may be a broadband light source and the optical reader 206 may employ a two dimensional array of pixels capturing a two dimensional image of the second sensing region 14. The control unit 212 may be configured to select specific regions of interest within the image of the second sensing region 14, analyze spectral content and surface topography of the regions of interest, determine porosity and depth variation of the regions of interest, algorithmically improve selectivity, dynamic range, and signal to noise of the primary signals of interest, that are otherwise degraded by variations in the detection region, residual sample turbidity and chemical interferents, for example.

The control unit 212 also obtains detection signals 214 from the sensor array 30 in the first sensing region of the diagnostic consumable 100 via the electrical contacts 204 and electrodes 32. For example, the detection signals 214 from the sensor array 30 may permit blood gas analysis of the blood sample as discussed above.

The control unit 212 can be constructed of circuitry and/or a combination of circuitry and software. It should also be understood that the control unit 212 need not be located within the diagnostic instrument 200 and can be located at an external location. For example, the diagnostic instrument 200 can be provided with a wireless transceiver to communicate with a control unit in a remote analysis unit.

Figure 2:
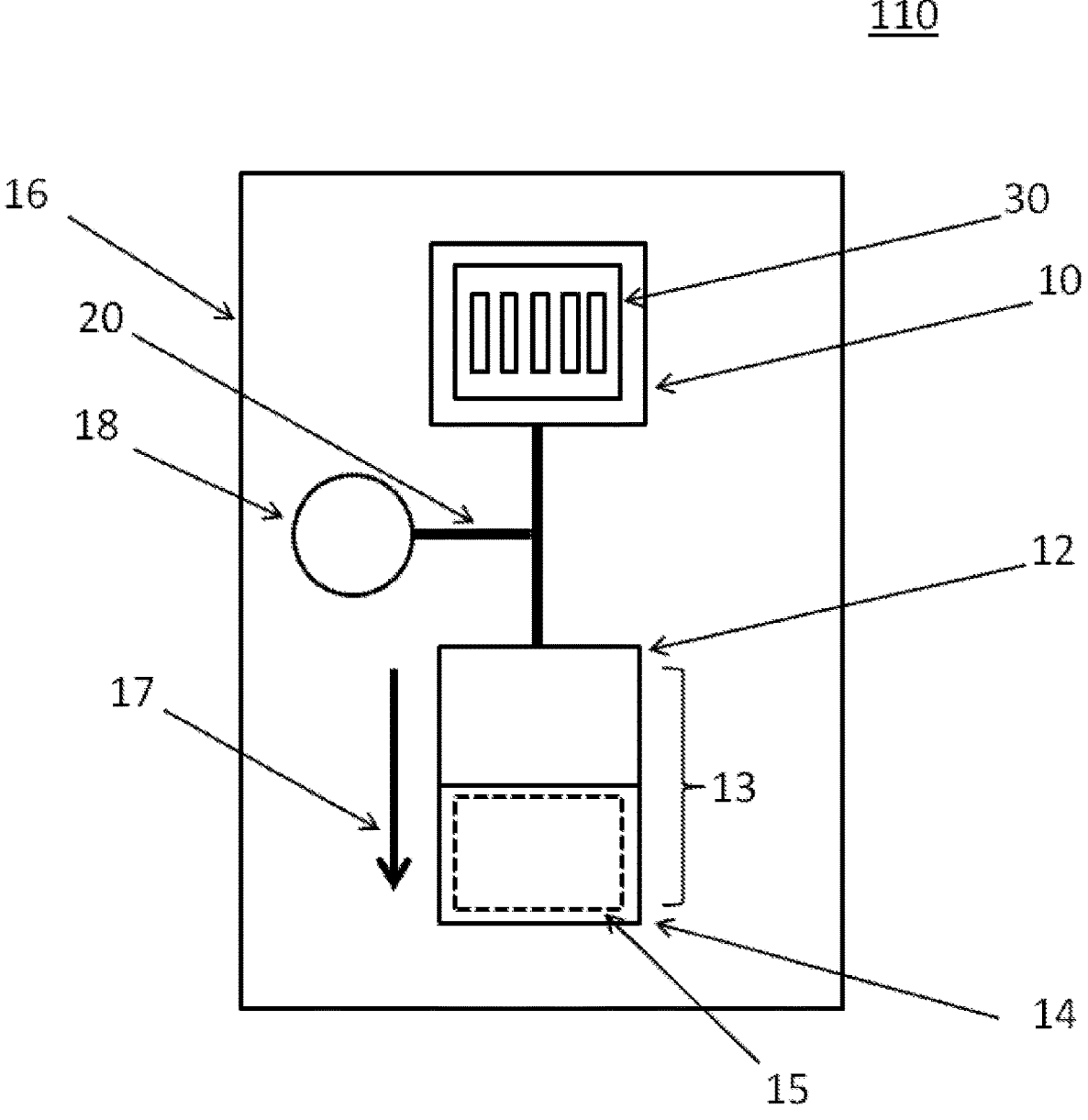
FIG. 2 is a plan view of a second example of a diagnostic consumable for use in the analysis of whole blood and plasma constructed in accordance with an embodiment of the present disclosure.

The whole blood sample may be introduced onto the diagnostic consumable 100 at one or more locations. For example, the whole blood sample may be introduced at a first sample application site (not shown) in fluid communication with the first sensing region 10 and a second sample application site (not shown) in fluid communication with the plasma separation membrane 12. However, in many cases it may be preferable to configure the diagnostic consumable so that the whole blood sample can be introduced onto the diagnostic consumable at a single location from which the whole blood sample is then distributed as needed on the diagnostic consumable. An example of a diagnostic consumable configured in this manner is shown in FIG. 2, which illustrates a diagnostic consumable 110 having a first sensing region 10, a plasma separation membrane 12, and a second sensing region 14 implemented on a substrate 16 similar to the diagnostic consumable 100 described above. Given the similarities between the diagnostic consumable 110 and the diagnostic consumable 100, in the interest of brevity only the differences are described herein. In the embodiment of FIG. 2, the diagnostic consumable 110 further includes a sample input port 18 for receiving a whole blood sample onto the diagnostic consumable 110, and sample distribution channels 20 for directing fluid flow on the diagnostic consumable. The sample distribution channels 20 are fluidically connected to the sample input port 18, the first sensing region 10 and the plasma separation membrane 12 so that a whole blood sample received at the sample input port 18 can be distributed into fluid contact with the first sensing region 10 and the plasma separation membrane 12.

The sample input port 18 may be configured to allow a blood sample delivery device, such as a syringe or capillary tube, to be coupled to the sample input port 18 to deliver a blood sample into the diagnostic consumable 110. For example, the sample input port 18 may include a gasket component (not shown) that facilitates a sealing engagement between the sample input port 18 and the sample delivery device. The gasket component may be a rubber or silicone component installed in the sample input port 18 and sized and shaped to sealingly engage a sample delivery device.

The sample distribution channels 20 may be formed on the substrate 16 in various manners. For example, the sample distribution channels 20 may be molded into the substrate 16 and/or may be formed via other additive (e.g., 3D printing) or subtractive (e.g., etching or machining) manufacturing techniques.

Figure 3:
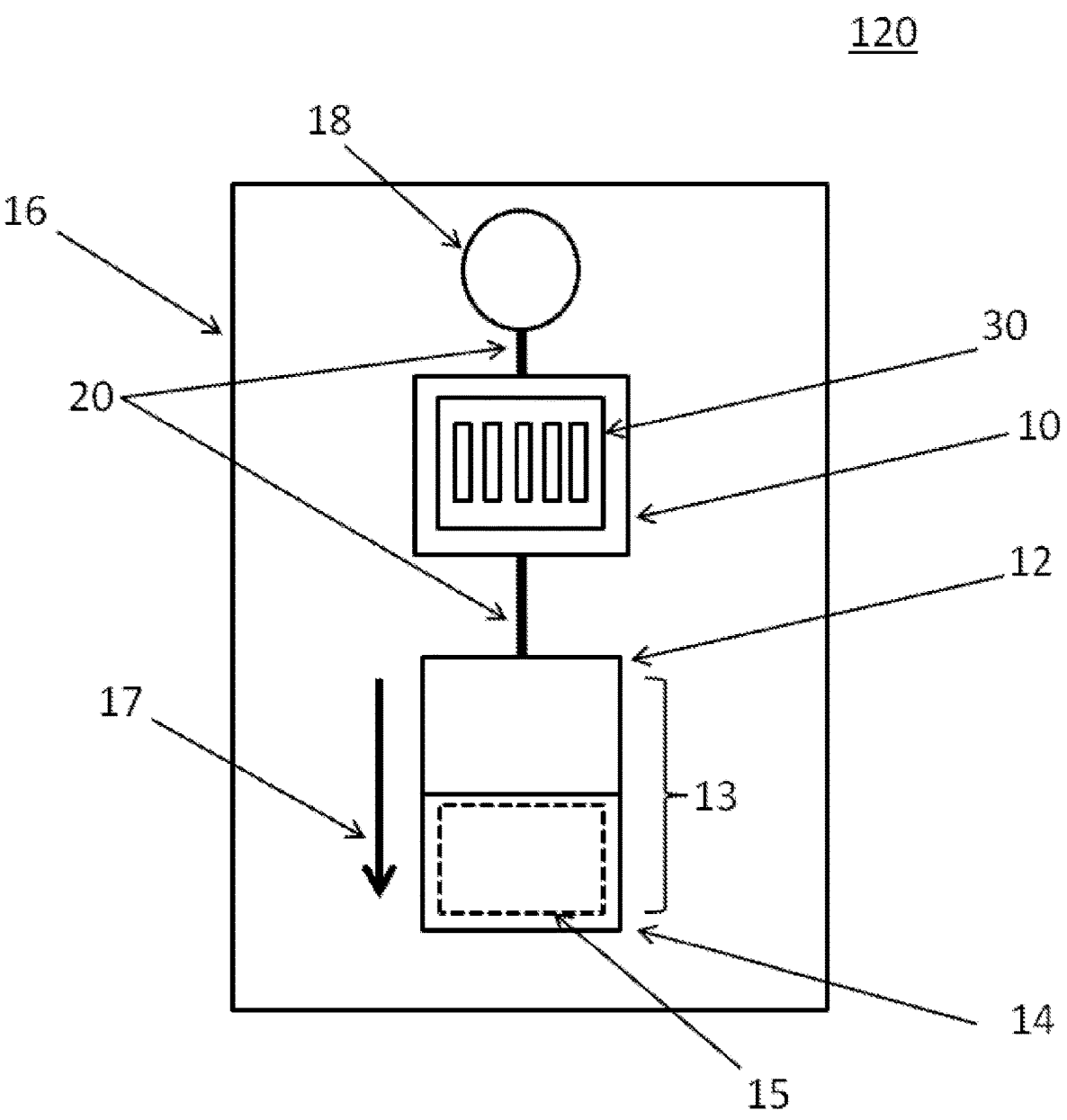
FIG. 3 is a plan view of a third example of a diagnostic consumable for use in the analysis of whole blood and plasma constructed in accordance with an embodiment of the present disclosure.

In the exemplary embodiment illustrated in FIG. 2, the diagnostic consumable 110 is configured such that the sample distribution channels 20 diverts a first portion of the whole blood sample received at the sample input port 18 to the first sensing region 10 for analysis of the whole blood sample, and diverts a second portion of the whole blood sample into fluidic contact with the plasma separation membrane 12 to produce the plasma sample for analysis in the second sensing region 14. In some cases, it may be preferable to configure a diagnostic consumable with the plasma separation membrane 12 and the second sensing region 14 fluidically connected downstream of the first sensing region 10 such that the portion of the whole blood sample that is brought into fluid contact with the plasma separation membrane 12 first passes through the first sensing region 10. For example, such an arrangement can potentially reduce the sample volume required to test the whole blood and plasma concurrently. Low sample volumes are particularly desirable when the blood sample that can safely be obtained is limited, such as in the case of whole blood samples from neonatal patients. An example of a diagnostic consumable configured in this manner is shown in FIG. 3, which illustrates a diagnostic consumable 120 having a sample input port 18, sample distribution channels 20, a first sensing region 10, a plasma separation membrane 12, and a second sensing region 14 implemented on a substrate 16 similar to the diagnostic consumable 110 described above and illustrated in FIG. 2. Given the similarities between the diagnostic consumable 120 and the diagnostic consumable 110, in the interest of brevity only the differences are described herein. In the embodiment of FIG. 3, the plasma separation membrane 12 is fluidically connected downstream of the first sensing region 14 relative to the sample input port 18. In particular, in the exemplary embodiment of FIG. 3 the sample distribution channels 20 include a first channel fluidically connected between the sample input port 18 and the first sensing region 10 and a second channel fluidically connected between the first sensing region 10 and the plasma separation membrane 12.

Figure 4:
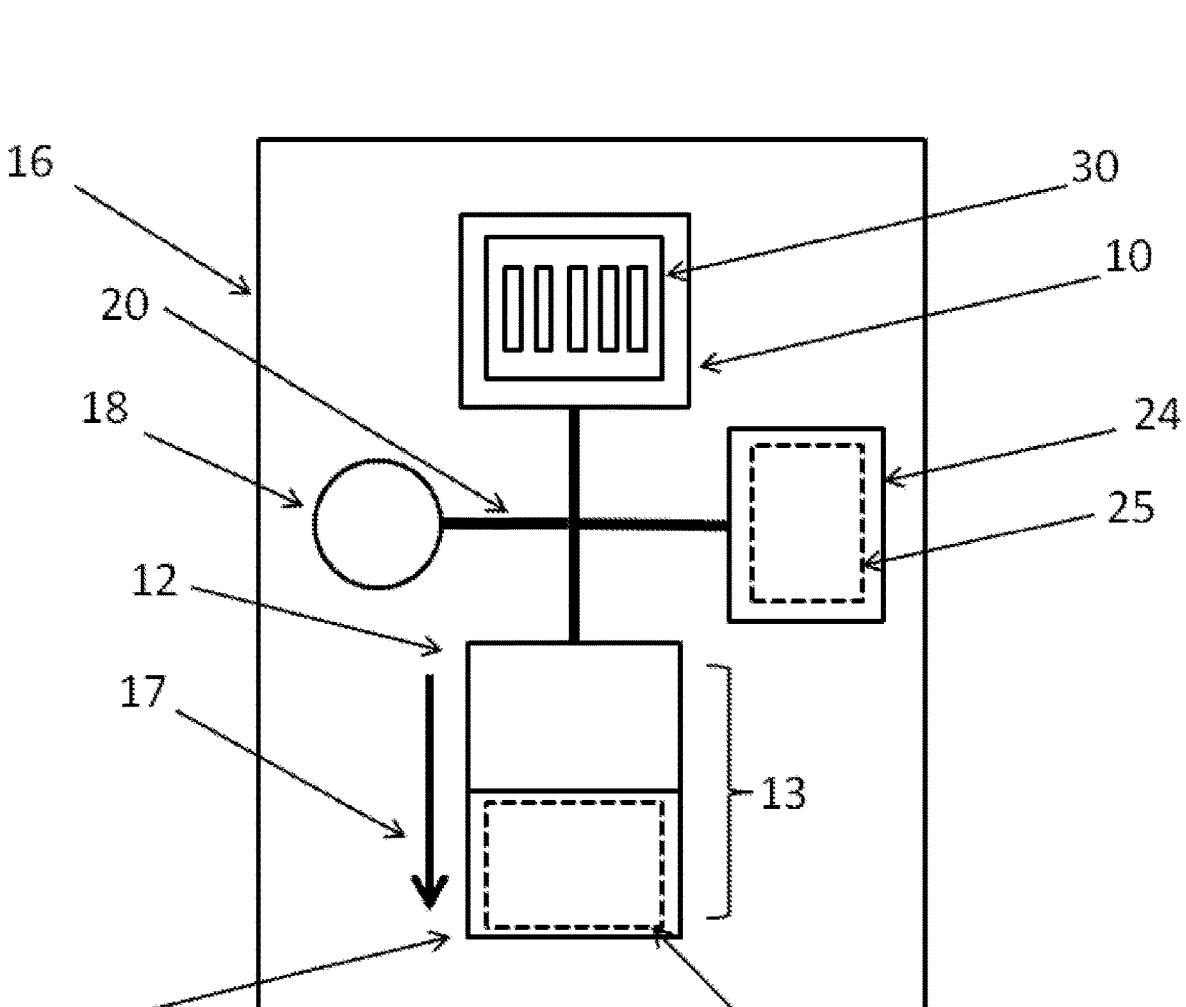
FIG. 4 is a plan view of a fourth example of a diagnostic consumable for use in the analysis of whole blood and plasma constructed in accordance with an embodiment of the present disclosure.

In the exemplary embodiments illustrated in FIGS. 1 to 3, analysis of the whole blood sample occurs in the first sensing region 10. In some embodiments, a diagnostic consumable constructed in accordance with the present disclosure may include one or more additional sensing regions for analysis of the whole blood sample. For example, in addition to assay(s) performed on the whole blood sample in the first sensing region 10 and assay(s) performed on the plasma sample in the second sensing region 14, in some embodiments one or more additional assays may be performed in one or more additional sensing regions on the diagnostic consumable. The additional assays performed in the additional sensing regions may be different from those performed in the first and second sensing regions. For example, assays using potentionmetric sensors may be performed on the whole blood sample in the first sensing region 10, and different assays, e.g., optical assays, may be performed on the whole blood sample in a third sensing region. An example of a diagnostic consumable configured in this manner is shown in FIG. 4, which illustrates a diagnostic consumable 130 having a sample input port 18, sample distribution channels 20, a first sensing region 10, a plasma separation membrane 12, and a second sensing region 14 implemented on a substrate 16 similar to the diagnostic consumable 110 described above and illustrated in FIG. 2. Given the similarities between the diagnostic consumable 130 and the diagnostic consumable 110, in the interest of brevity only the differences are described herein. In the embodiment of FIG. 4, the diagnostic consumable 130 further includes a third sensing region 24 that is fluidically connected to the sample input port 18 via the sample distribution channels 20. In the illustrated embodiment, the third sensing region 24 is configured for an analysis of the whole blood sample that differs from the analysis for which the first sensing region 24 is configured. In particular, on the diagnostic consumable 130, the first sensing region 10 includes a sensor array 30 as described above, and the third sensing region 24 is configured for an optical assay of the whole blood sample. In particular, at least a portion 25 of the third sensing region 24 is optically transparent so as to permit an optical assay within the third sensing region. For example, the third sensing region 24 might include a hemolysis channel (not shown) having disposed thereon a hemolytic reagent for hemolyzing a portion of the whole blood sample to generate a hemolyzed blood sample, and a chamber (not shown) configured for containing at least a portion of the hemolyzed blood sample for an optical assay. For example, such an optical assay could include performing an optical assay of the hemolysed blood in the chamber through at least a portion of the chamber that is optically transparent. For example, the chamber could have optically transparent top and bottom surfaces and performing the optical assay could involve performing a spectroscopic analysis of light passed through the hemolysed blood in the chamber via the optically transparent top and bottom surfaces of the chamber. Such an optical assay could be a co-oximetry assay to measure the concentrations of total hemoglobin (tHb), oxyhemoglobin (O2HB), carboxyhemoglobin (COHb), methemoglobin (MetHb), deoxyhemoglobin (HHb), oxygen saturation (SO2) and/or total bilirubin (tBili) in the blood sample, for example.

Further detailed examples of diagnostic consumables incorporating first, second and third sensing regions similar to the diagnostic consumable 130 of FIG. 4 will now be described with reference to FIGS. 5 to 9. It is to be understood that these example implementations are provided for illustrative purposes only, and that other implementations and configurations of multiple sensing regions permitting analysis of whole blood and plasma on a diagnostic consumable are possible and are contemplated within the present disclosure.

Figure 5:
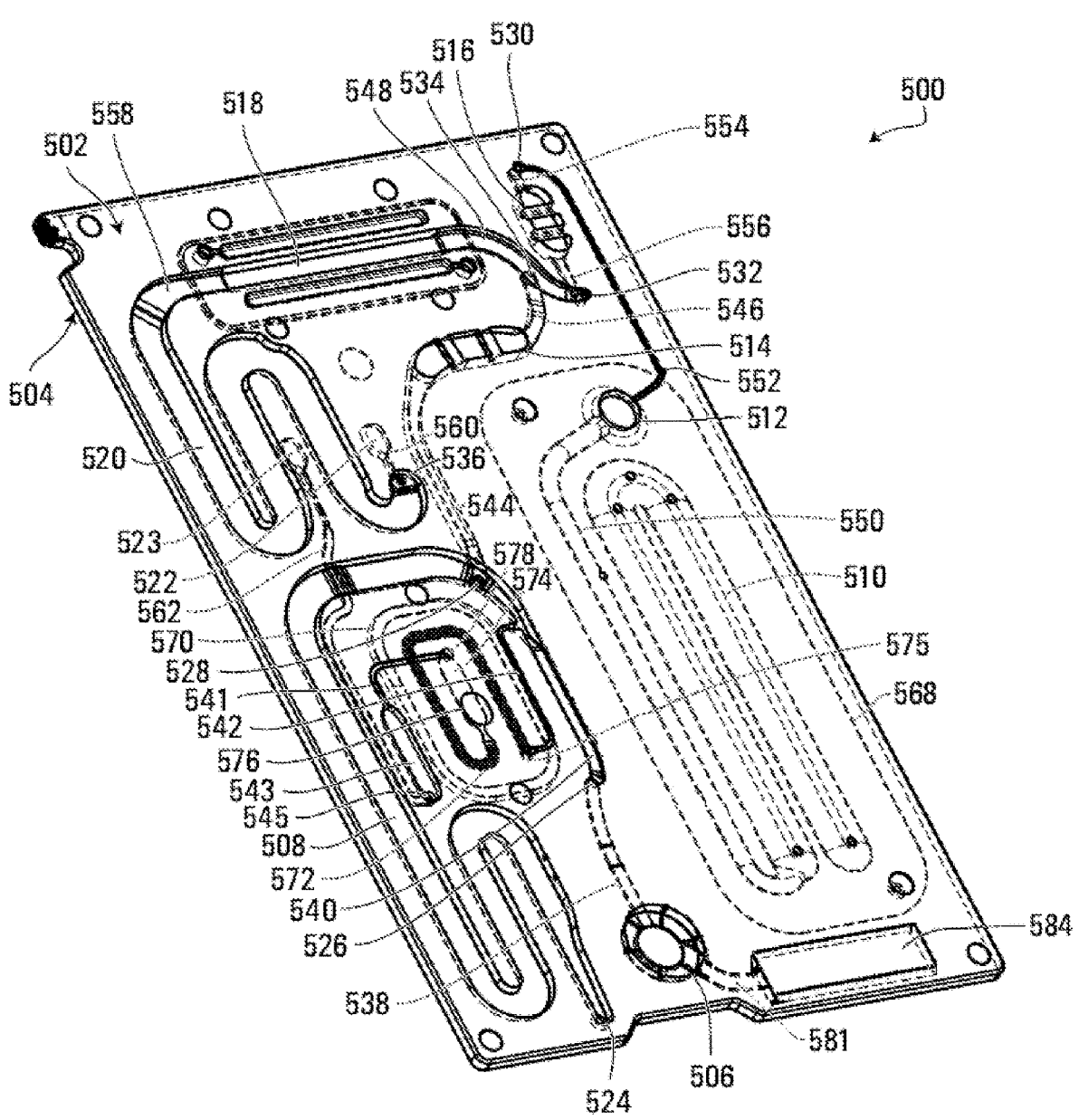
FIG. 5 is an isometric view of the top of an example of a substrate for a diagnostic consumable for use in the analysis of whole blood and plasma constructed in accordance with an embodiment of the present disclosure.
Figure 6:
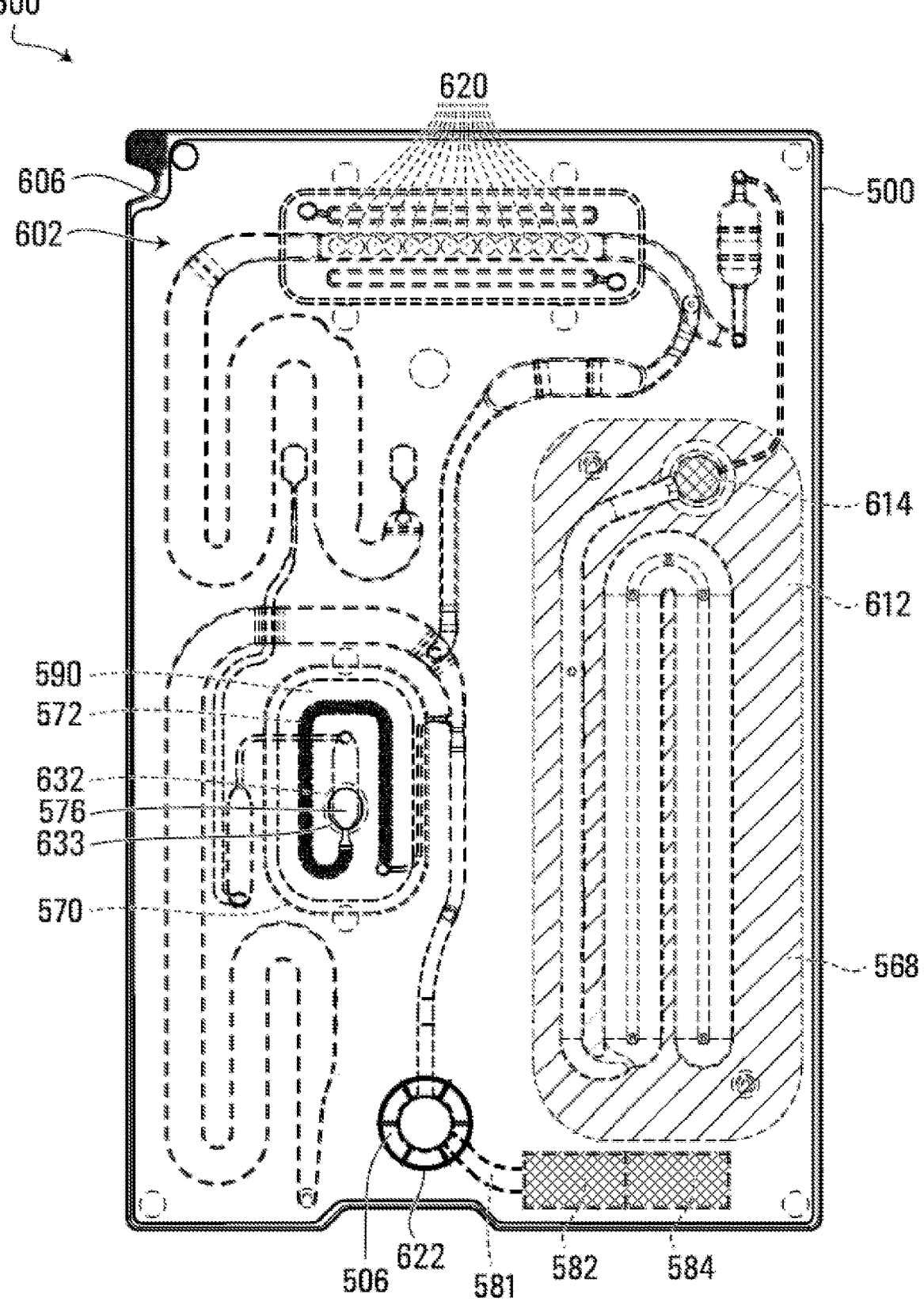
FIG. 6 is a plan view of the top of a diagnostic consumable incorporating the substrate of FIG. 5.
Figure 7:
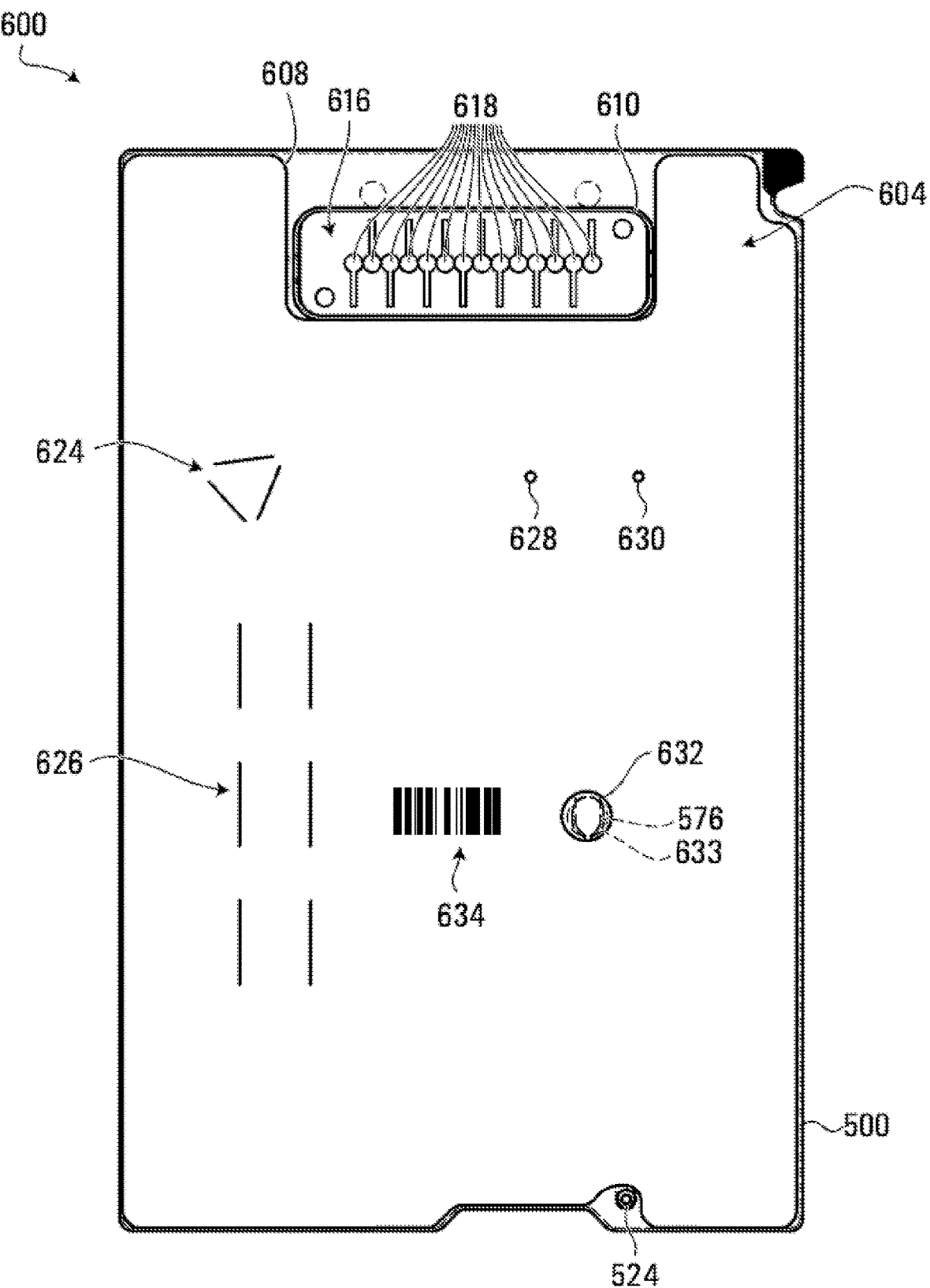
FIG. 7 is a plan view of the bottom of the diagnostic consumable of FIG. 6.

FIG. 5 is an isometric view of a substrate 500 for a diagnostic consumable that include multiple sensing regions in accordance with embodiments of the present disclosure. FIGS. 6 and 7 are top and bottom plan views, respectively, of a diagnostic consumable 605 incorporating the substrate 500. The terms "top" and "bottom" are used herein for ease of reference only, and do not require or imply a certain orientation of the substrate 500. Although the substrate 500 could be designed to be operated with its top surface facing vertically upwards and its bottom surface facing vertically downwards, this might not be the case in all implementations.

Referring first to the substrate 500 illustrated in FIG. 5, the substrate 500 is illustrated as being a rectangular prism that is approximately the size and shape of a credit card, but this is only an example. The substrate 500 could also or instead be other shapes such as triangular or circular, for example. The substrate 500 could be made out of plastics, ceramics, glass and/or metal, for example. The substrate 500 could be a single, unitary body or part. The dimensions of the substrate 500 are not limited to any specific ranges or values. In some implementations, the length and/or width of the substrate 500 is on the order of centimeters. Other lengths and/or widths of the substrate 500 are also possible. The thickness of the substrate 500 could be measured as the distance between a top surface 502 and a bottom surface 504 of the substrate. In some implementations, the thickness of the substrate 500 is on the order of millimeters. Other thicknesses of the substrate 500 are also possible. Although the top surface 502 and the bottom surface 504 of the substrate 500 are illustrated as being substantially flat, this might not be the case in all embodiments. For example, the top surface and/or the bottom surface of a substrate could also or instead be triangular, conical and/or hemispherical in shape. Accordingly, the thickness of a substrate could vary along its length and/or width. The substrate 500 is illustrated as being transparent, however substrates could also or instead be, in whole or in part, translucent or opaque. The terms "top" and "bottom" are used herein for ease of reference only, and do not require or imply a certain orientation of the substrate 500. Although the substrate 500 could be designed to be operated with the top surface 502 facing vertically upwards and the bottom surface 504 facing vertically downwards, this might not be the case in all implementations.

The substrate 500 includes a sample fluid input port 506, a sample fluid reservoir 508, a fluid reservoir 510, a valve hole 512, two bubble traps 514, 516, a first sensing region 518, a second sensing region 584, a third sensing region 570, waste fluid reservoirs 520, 543, multiple pump connection ports 522, 523, multiple vias 112, 114, 524, 526, 528, 530, 532, 534, 536, 545, 575, 578, and multiple channels 538, 540, 541, 542, 544, 546, 548, 550, 552, 554, 556, 558, 560, 562, 581. In FIG. 5, solid lines are used to illustrate components that are directly in view in each figure, and dashed lines are used to illustrate components that are hidden from view by at least a portion of the substrate 500.

The channels 538, 540, 541, 542, 544, 546, 548, 550, 552, 554, 556, 558, 560, 562, 581 are provided to carry one or more fluids in the substrate 100. The channels 540, 541, 542, 548, 552, 558 are trenches or grooves in the top surface 502 of the substrate 500. The channels 540, 541, 542, 548, 552, 558 are illustrated as being open at the top surface 502 of the substrate 500 in FIG. 5. Similarly, the channels 538, 544, 546, 550, 554, 556, 560, 562, 581 are trenches or grooves in the bottom surface 504 of the substrate 500, which are open at the bottom surface of the substrate.

The vias 524, 526, 528, 530, 532, 534, 536, 545, 575, 578 are through-holes or bores that extend through the substrate 500. Vias could be used to fluidly connect two or more components of the substrate 500. For example, via 575 fluidly connects channel 542 and a hemolysis channel 572 in the third sensing region 570. Vias could also or instead be used to fluidly connect a component of the substrate 500 to the top surface 502 and/or bottom surface 504 of the substrate. For example, the via 524 fluidly connects the sample fluid reservoir 508 to the bottom surface 504 of the substrate 500.

The sample fluid input port 506 is provided to deliver a blood sample to the substrate 500. In the exemplary embodiment, the sample input port 506 is a conical or cylindrical opening in the top surface 502 of the substrate 500. The sample input port 506 is coupled to the channel 538 and the channel 581. The sample input port 506 could be sized and shaped to engage with an end of a blood sample delivery device, such as a syringe or capillary tube (not shown), that delivers the blood sample. For example, in the case of a syringe, this engagement between the sample input port 506 and the syringe could form a seal such that, when the blood sample is propelled or pumped out of the syringe, the blood sample is forced into the channels 538 and 581 and does not spill out of the sample input port. In some embodiments, a gasket component is installed in the sample input port 506 in order to facilitate the sealing engagement with the sample delivery device.

The sample fluid reservoir 508 could be a relatively wide and long channel or chamber that is coupled to the channel 540. The sample fluid reservoir 508 is illustrated with a rectangular cross-section, however other cross-sectional shapes are also possible. The sample fluid reservoir 508 could be provided to store part of a blood sample after it is delivered into the substrate 500. The via 524 could act as an air vent to allow air to escape the sample fluid reservoir 508 when it is displaced by the addition of blood sample.

The fluid reservoir 510 could be a relatively wide and long channel or chamber that is coupled to the channel 550. The fluid reservoir 510 is illustrated as a U-shaped channel with a semicircular cross-section, however other geometries are also possible. The fluid reservoir 510 could be provided to store a calibration fluid or a wash fluid and/or a fluid pack that seals the calibration fluid or the wash fluid. In embodiments where the fluid stored in the fluid reservoir 510 is a calibration fluid, the calibration fluid could be used to calibrate one or more sensors included on and/or coupled to the substrate 500 in the first sensing region 518. Calibration fluids could include fluids with known concentrations of one or more analytes. These analytes could correspond to analytes in the blood sample that might be measured using sensors in the first sensing region 518 of the substrate 500. In embodiments where the fluid reservoir 510 stores a wash fluid, the wash fluid could be used to wash one or more regions of the substrate 500. For example, the wash fluid could be used to wash away unbound components from an antigen-antibody interaction region.

The valve hole 512 could be a via or bore that extends through the thickness of the substrate 500. The channel 550 and the channel 552 could be fluidly connected by the valve hole 512. The valve hole 512 could be sized and shaped to accommodate and/or couple to a valve (not shown). This valve could control the flow of fluid from the channel 550 to the channel 552. When the valve is closed, the flow of fluid between the channel 550 and the channel 552 could be blocked. When the valve is opened, the flow of fluid between the channel 550 and the channel 552 could be permitted. In some implementations, the valve could be closed until a seal in the valve is ruptured, allowing fluid to flow into the channel 552.

The two bubble traps 514, 516 are provided to inhibit the movement of bubbles in the substrate 500. Each bubble that enters either of the bubble traps 514, 516 could be prevented from moving further downstream by one or more barriers in the bubble trap. The bubble trap 514 fluidly connects the channels 544, 546, and the bubble trap 516 fluidly connects the channels 554, 556. One or both of the bubble traps 514, 516 may be omitted in some embodiments.

The first sensing region 518 includes a channel that is coupled to the channel 548 and to the channel 558. The first sensing region 518 extends through the thickness of the substrate 500, and is therefore illustrated as being open at the top surface 502 and bottom surface 504 of the substrate in FIG. 5. The first sensing region 518 could include and/or be coupled to one or more sensors that measure properties of fluids in the sensing region. For example, the sensors could measure the concentration of one or more analytes in a fluid that flows from the channel 548 to the channel 558.

The waste fluid reservoir 520 is fluidly coupled to the channel 558, and stores fluid that has flowed through the first sensing region 518. The waste fluid reservoir 520 is illustrated as a meandering channel with a rectangular cross-section; however other geometries of the waste fluid reservoir 520 are also possible.

The second sensing region 584 is coupled to the sample input port 506 through channel 581. The second sensing region 584 extends through the thickness of the substrate 500, and is therefore illustrated as being open at the top surface 502 and bottom surface 504 of the substrate in FIG. 5. In some embodiments, the second sensing region 584 may not extend all the way through the thickness of the substrate 500, such that either the top portion or the bottom portion of the second sensing region 584 is closed by the substrate itself. The second sensing region 584 could include and/or be coupled to a plasma separation membrane that separates plasma from blood cells to generate a plasma sample for analysis in the second sensing region 584.

The pump connection ports 522, 523 provide a connection to one or more external pumping systems. For example, these pumping systems could be provided in a diagnostic instrument, such as a portable diagnostic consumable reader. The channel 560 is fluidly connected to the pump connection port 522, and the channel 562 is fluidly connected to the pump connection port 523. The pumping systems could include channels or tubes that fluidly connect to the pump connection ports 522, 523. In some embodiments, the pumping systems could include vacuum pumping systems that pull fluid in one or more channels of the substrate 500 towards the pump connection ports 522, 523.

The third sensing region 570 provides another sensing functionality to a diagnostic consumable incorporating the substrate 500. In the exemplary embodiment, the third sensing region includes a hemolysis channel 572 and a chamber 574 fluidly connected to the hemolysis channel. At least a portion 576 of the chamber 574 is optically transparent to permit an optical assay of fluid within the chamber. The channel 542 fluidly connects the channel 540 to the hemolysis channel 572 through via 575. The channel 541 fluidly connects the chamber 574 and a waste fluid reservoir 543 through via 545. The channel 562 fluidly connects the waste fluid reservoir 543 to the pump connection port 523 through via 578, In operation, as will be discussed in further detail below, at least a portion of a blood sample could be directed through the channel 542, the hemolysis channel 572 and into the chamber 574 to be optically analyzed in the third sensing region 570.

FIGS. 6 and 7 illustrate plan views of an example diagnostic consumable 600 that incorporates the substrate 500 shown in FIG. 5. The diagnostic consumable 600 could be considered an assembled diagnostic card or test card for blood analysis and/or testing. The diagnostic consumable 600 could be configured, by being sized and shaped for example, to be received by a diagnostic instrument such as a portable diagnostic consumable reader (not shown). FIG. 6 is a view of the top surface 602 of the diagnostic consumable 600, and FIG. 7 is a view of the bottom surface 604 of the diagnostic consumable. In addition to the substrate 500, the device 600 includes a cover layer 590 covering the third sensing region 570, a top cover layer 606, a bottom cover layer 608, a sensor array 610 in the first sensing region 518, a plasma separation membrane 582 (illustrated using cross-hatching), a calibration fluid pack 612 (illustrated using parallel hatching), a valve 614 (illustrated using cross-hatching). Many components of the substrate 500 are not labeled in FIGS. 6 and 7 for the purpose of clarity.

As described earlier, a hemolytic reagent, such as a surfactant/detergent dissolved in water and isopropyl alcohol, may be deposited and dried-down on the hemolysis channel 572 before the cover layer 590 is affixed to the substrate 500. In some embodiments, the hemolysis channel 572 may include structures, such as micro-projections, that increase the surface area of the channel. In this example, the cover layer 590 is transparent to facilitate optical sensing within the chamber 574 downstream of the hemolysis channel. For example, the cover layer 590 may be made from a material with relatively high optical transparency, such as glass or polymethyl methacrylate (PMMA), also known as acrylic or acrylic glass. In other embodiments, a cover layer for a hemolysis stage could be transparent, translucent, opaque, or a combination thereof.

At least a portion of the top surface 502 and bottom surface 504 of the substrate 500 are sealed using the top cover layer 606 and the bottom cover layer 608, respectively.

The top and bottom cover layers 606, 608 could be impermeable to liquids (and possibly gases) to provide a liquid tight (and possibly gas tight) seal. In some implementations, the top and bottom cover layers 606, 608 could include plastic, metal and/or ceramic films that are bonded to the substrate 500 using an adhesive. For example, in some implementations, the top cover layer 606 and/or the bottom cover layer 608 could be implemented as an adhesive label or sticker. Non-limiting examples of adhesives include acrylic adhesives and silicone adhesives. The top and bottom cover layers 606, 608 could form a seal around one or more components of the substrate 500. For example, the top cover layer 606 could seal, at least in part, the sample fluid reservoir 508, the bubble traps 514, 516, the first sensing region 518, the plasma separation membrane 582, the second sensing region 584, the waste fluid reservoir 520 and the channels 540, 541, 542, 548, 552, 558. The bottom cover layer 608 could seal, at least in part, the sample input port 506, the fluid reservoir 510, the bubble traps 514, 516, the plasma separation membrane 582, the second sensing region 584, and the channels 538, 544, 546, 550, 554, 556, 560, 562. The top cover layer 606 is illustrated as being substantially transparent and the bottom cover layer 608 is illustrated as being substantially opaque, but this is only an example. In general, either or both of the top cover layer 606 and the bottom cover layer 608 could be transparent, translucent, opaque, or a combination thereof. In FIG. 6, dashed lines are used to illustrate components that are under the top cover layer 606.

In this example, the sensor array 610, which could also be referred to as an electrode module, is bonded to the bottom surface 504 of the substrate 500. The sensor array 610 overlaps and seals at least a portion of the first sensing region 518. The bottom cover layer 608 does not overlap the sensor array 610. In this example, the sensor array 610 includes a metal foil laminated to an epoxy foil element 616 with an optional adhesive. The metal foil is formed into an array of electrode elements 618. Each electrode element 618 could have a connection end for forming an electrical connection to a measuring circuit in a diagnostic instrument, for example. Multiple sensors 620 are coupled to the electrode elements 618. Each of the sensors 620 are positioned over the first sensing region 518 of the substrate 500. In use, the sensors 620 could be used to measure one or more properties of a calibration fluid and/or a blood sample in the first sensing region 518 as described earlier.

The calibration fluid pack 612 is sandwiched between the calibration fluid pack region 568 of the substrate 500 and the bottom cover layer 608. The calibration fluid pack 612 could be provided to seal and store a calibration fluid, in order to improve the stability of the calibration fluid over time. For example, the calibration fluid pack 612 could inhibit gases, such as carbon dioxide, from permeating into and/or out of the calibration fluid.

In the exemplary embodiment, the top surface 502 of the substrate 500 is substantially sealed by the top cover layer 606, with the exception of a hole 622 that corresponds to the location of the sample input port 506. The hole 622 allows a blood sample delivery device, such as a syringe or capillary tube, to be coupled to the sample input port 506 to deliver a blood sample into the diagnostic consumable 600. In addition, the top cover layer 606 also includes a second hole 633 that corresponds to the location of the optical sensing portion 576 of the third sensing region 570.

The bottom surface 504 of the substrate 500 is substantially covered by the bottom cover layer 608. However, the sensor array 610 and via 524 are not sealed by the bottom cover layer. The bottom cover layer 608 includes cuts or scoring 624, 626. The scoring 624, 626 could be provided to render the bottom cover layer 608 more malleable and workable in the area proximate the scoring. The position of the scoring 624 corresponds to the position of the valve 614. The scoring 624 could make the portion of the bottom cover layer 608 that is adjacent to the valve 614 more flexible, and could therefore permit the valve to be manipulated more easily. The position of the scoring 626 corresponds to the position of the fluid reservoir 510. The scoring 626 could make the portion of the bottom cover layer 608 adjacent to the fluid reservoir 510 more flexible, and therefore permit the calibration fluid pack 612 to be manipulated more easily. The bottom cover layer 608 also includes pump holes 628, 630 corresponding to the location of the pump connection ports 522, 523 on the substrate 500. The pump connection ports 522, 523 could be connected to a pump in a card reader module through the pump holes 628, 630. The pump holes 628, 630 could be sized and shaped to form a seal between the pump and the pump connection ports 522, 523. The bottom cover layer 608 overlaps the cover layer 590 of the third sensing region 570, but includes a hole 632 corresponding to the optical sensing portion 576 and generally aligned with the hole 633 in the top cover layer 606. The holes 632, 633 and the transparency of the substrate 500 and the cover layer 590 in the area of the optical sensing portion 576 of the third sensing region facilitate optical sensing.

In the exemplary embodiment, the top cover layer 606 is substantially optically transparent, and therefore certain optical assays, such as a colorimetric analysis of a plasma sample in the second sensing region 584 may be conducted through the top cover layer 606. However, in some embodiments, a separate optically transparent cover layer, similar to the cover layer 590 for the third sensing region 570, may be coupled to the substrate 500 to cover the second sensing region 584, and the top and bottom cover layers 606, 608 may include holes substantially aligned with the second sensing region 584 to facilitate optical sensing of the plasma sample in the second sensing region 584.

In this example, a 1D barcode 634 is printed on the bottom cover layer 608. The barcode 634 could be read by a diagnostic instrument when the diagnostic consumable 600 is inserted into the instrument. The barcode 634 could authenticate the diagnostic consumable 600 and/or provide information regarding the diagnostic consumable. For example, the barcode 634 could indicate the date that the diagnostic consumable 600 was manufactured. The barcode 634 is one example of a machine-readable code that could be present on the bottom cover layer 608 or elsewhere on the diagnostic consumable. Other examples of machine-readable codes include 2D barcodes. Radio-frequency identification (RFID) chips or tags could also or instead be used.

In some embodiments, the diagnostic consumable 600 could be operated as follows. First, the diagnostic consumable 600 could be inserted into a corresponding slot of a diagnostic instrument, such as a portable or bench-top diagnostic card reader. The diagnostic instrument might scan the barcode 634 to authenticate the diagnostic consumable 600. Second, the calibration fluid that is stored in the calibration fluid pack 612 could be propelled or pumped into the sensing region 618. This step could include the diagnostic instrument using a first actuator element to manipulate the valve 614 by pushing on the bottom cover layer 608 in an area proximate the scoring 624. The manipulation of the valve 614 could cause the plug in the valve to rupture, which opens the valve. At least a portion of the calibration fluid could then be pushed or pumped out of the calibration fluid pack 612, through the channel 550, the valve 512, the channel 552, the via 530, the channel 554, the bubble trap 516, the channel 556, the via 532, the channel 548, and into the first sensing region 518. Pushing the calibration fluid out of the calibration fluid pack 612 could be performed by compressing the bottom cover layer 608 in the area proximate the scoring 626 using a second actuator element, such as a plunger, in the diagnostic instrument. When the calibration fluid is in the first sensing region 518, it might be in contact with one or more of the sensors 620. The diagnostic instrument could include circuitry to contact the electrodes 618, which return measurements of the calibration fluid from the sensors 620. These measurements could be used to calibrate the diagnostic instrument for the diagnostic consumable 600, and thereby compensate for variations between different diagnostic consumables. The first and second actuator elements could be controlled by a motor-driven system in the diagnostic instrument. The diagnostic instrument could also include a form of temperature control, such as a heater in contact with the sensor array 610, to adjust the temperature of a fluid in the first sensing region 518 and/or a heater in contact with, or proximal to, the second sensing region 582 or the third sensing region 570. This temperature control could help provide consistency in the measurements made by the sensors 620 in the first sensing region 518 or by optical sensor(s) in the diagnostic instrument configured to measure one or more properties of a sample in the second sensing region 582 or the third sensing region 370. In some implementations, the temperature control may be applied to achieve a fluid temperature of approximately body temperature, e.g., at approximately 37 degrees Celsius.

After calibration, the diagnostic instrument could instruct a user to inject a blood sample into the sample fluid input port 506. A first portion of the blood sample could flow through the channel 538, the via 526, the channel 540 and into the sample fluid storage reservoir 508. A second portion of the blood sample could flow through the channel 581 and into fluid contact with the plasma separation membrane 582, which separates plasma from blood cells. The separated plasma sample then flows into the second sensing region 584. The plasma sample in the second sensing region 584 may then be analyzed by eye or analyzed by machine using an optical reader as described previously.

A vacuum pump in the diagnostic instrument could be coupled to the pump connection port 522 through the pump hole 628. When this vacuum pump is turned on, the vacuum pump could draw the calibration fluid from the first sensing region 518 into the waste fluid reservoir 520. Further, the vacuum pump could draw the blood sample from the sample fluid reservoir 508 and/or the channel 540 (if the fluid reservoir 508 is not vented), through via 528, the channel 544, the bubble trap 514, the channel 546, via 534, the channel 548, and into the first sensing region 518. The diagnostic instrument and sensors 620 could then perform measurements on the blood sample to determine the concentration of certain analytes in the blood sample as described earlier.

Optical assays can be performed on the blood sample in the optical sensing portion 576 of the third sensing region 570. For example, a vacuum pump in the diagnostic instrument that is coupled to the pump connection port 523 through the pump hole 630 could be used to apply vacuum pressure to the pump connection port 523 to draw a portion of the blood sample from the sample fluid reservoir 508 and/or the channel 540, through the channel 542, the via 575, the hemolysis channel 572, and into the chamber 574.

As the blood sample is flowed through the hemolysis channel 572, it dissolves, re-suspends, and reacts with the hemolytic reagent that was dried-down on the hemolysis channel 572 to generate hemolysed blood, which is then dispensed into the chamber 574. A light source and optical reader in the diagnostic instrument could then perform optical measurements, such as CO-oximetry measurements, on the hemolysed blood sample in the optical sensing portion 576 of the chamber 574. This could complete the testing that is performed using the diagnostic consumable 600. In this exemplary embodiment, the diagnostic consumable 600 is a disposable diagnostic device that is disposed of after a single-use. However, reusable devices are also contemplated.

Figure 8:
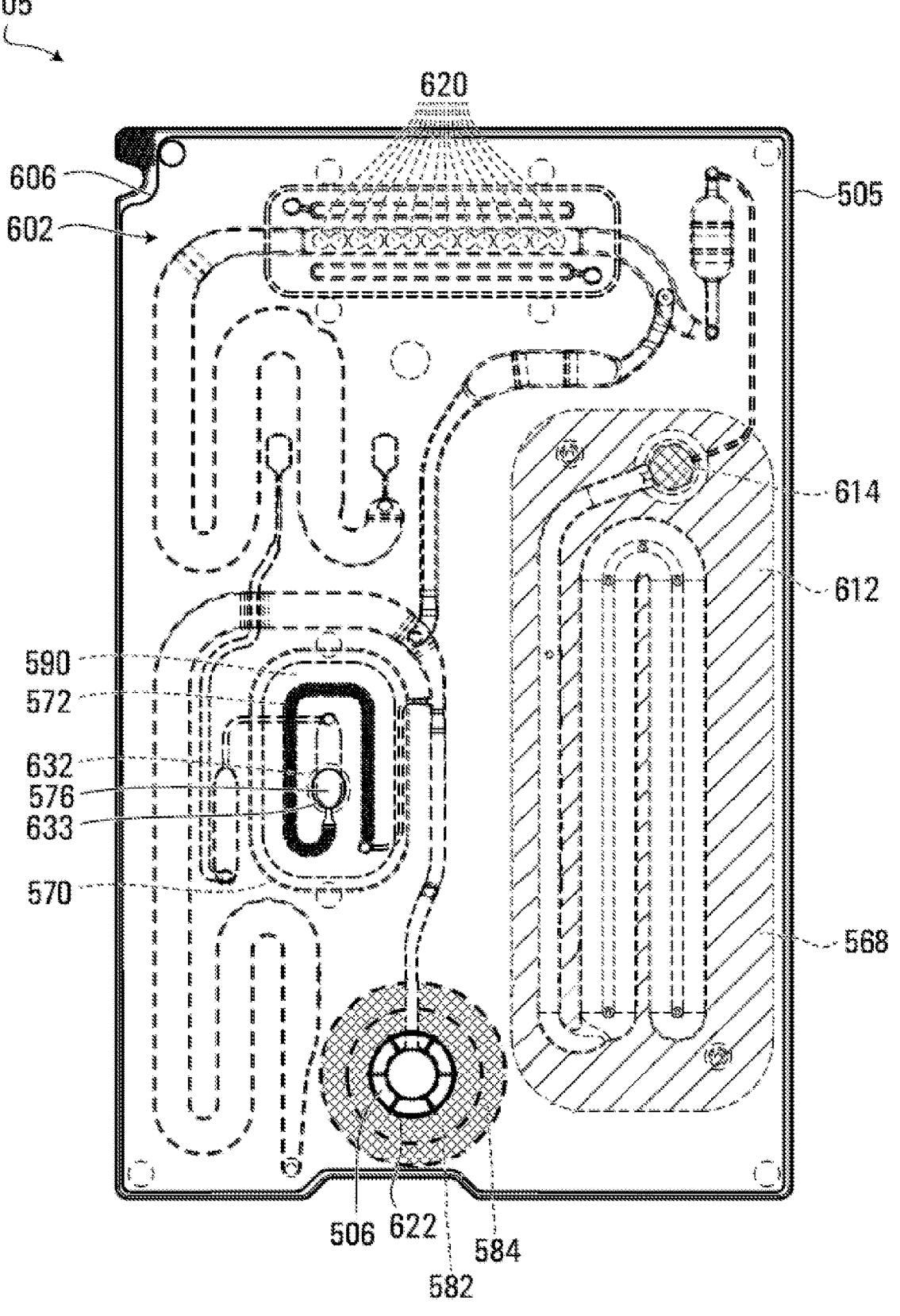
FIG. 8 is a plan view of the top of another example of a diagnostic consumable for use in the analysis of whole blood and plasma constructed in accordance with an embodiment of the present disclosure.

FIG. 8 is a top plan view of another example of a diagnostic consumable 605 constructed in accordance with an embodiment of the present disclosure. The diagnostic consumable 605 incorporates a substrate 505. The diagnostic consumable 605 and the substrate 505 are similar to the diagnostic consumable 600 and the substrate 500 described above and therefore in the interest of brevity only the differences are described herein. In the embodiment of FIG. 8, the plasma separation membrane 582 and the second sensing region 584 substantially surround the sample input port 506. One or more channels or openings (not shown) may provide fluid communication between the sample input port and one or more locations on the plasma separation membrane 582.

Figure 9:
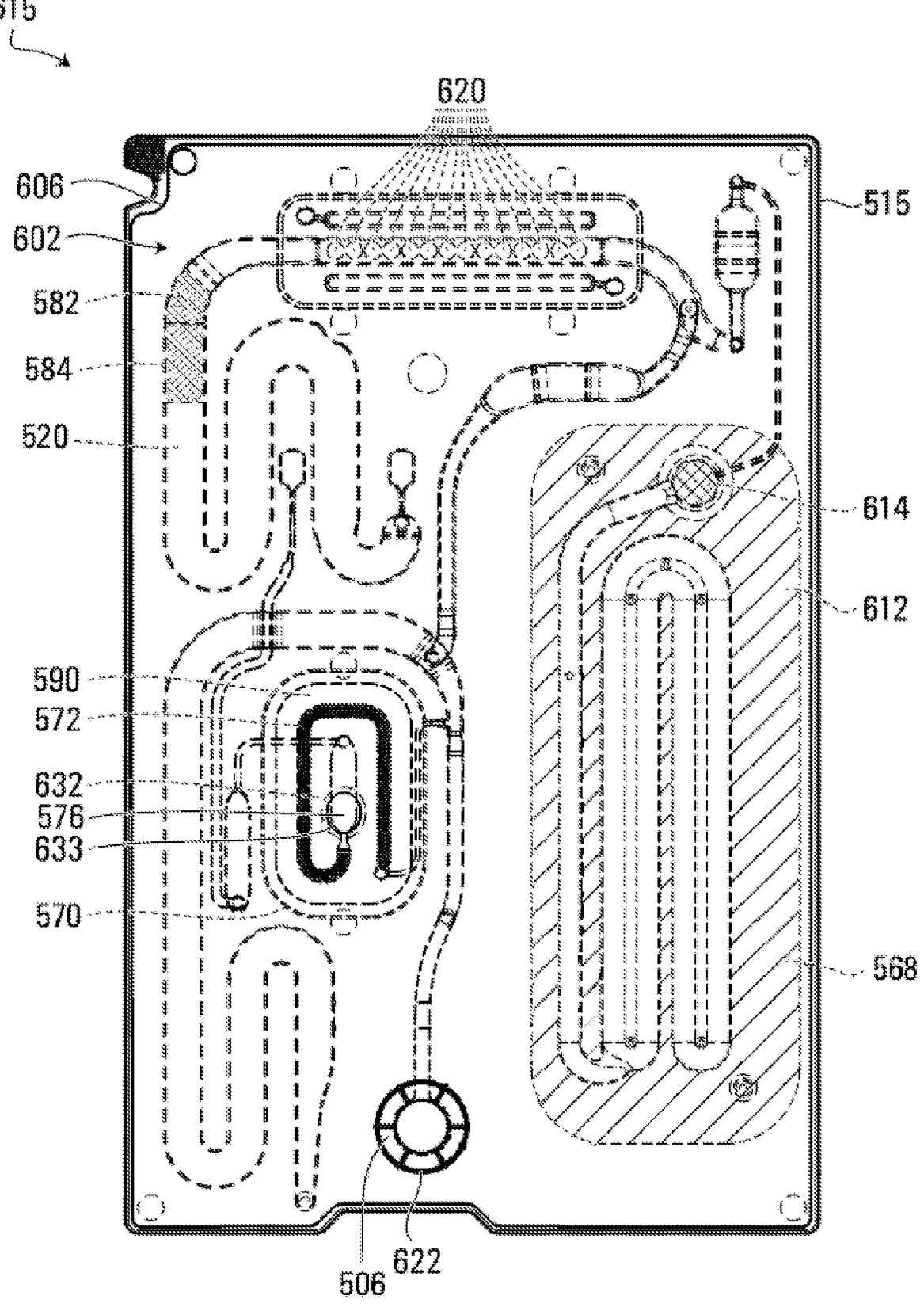
FIG. 9 is a plan view of the top of yet another example of a diagnostic consumable for use in the analysis of whole blood and plasma constructed in accordance with an embodiment of the present disclosure.

FIG. 9 is a top plan view of another example of a diagnostic consumable 615 constructed in accordance with an embodiment of the present disclosure. The diagnostic consumable 615 incorporates a substrate 515. The diagnostic consumable 615 and the substrate 515 are similar to the diagnostic consumable 600 and the substrate 500 described above and therefore in the interest of brevity only the differences are described herein. In the embodiment of FIG. 9, the plasma separation membrane 582 and the second sensing region 584 are arranged in the waste fluid reservoir 520 after the sensor array 610 of the first sensing region 518. In this way the configuration of the first sensing region 518, the plasma separation membrane 582 and the second sensing region 584 of the diagnostic consumable 615 is similar to the arrangement of the first sensing region 10, the plasma separation membrane 12 and the second sensing region 14 of the diagnostic consumable 120 shown in FIG. 3.

Although many of the example embodiments discussed above relate primarily to evaluating whole blood and plasma on diagnostic consumables for blood analysis systems, the embodiments described herein could also or instead relate to other types of fluid sample analyses in diagnostic consumables or other types of analysis systems. In particular, fluid transport materials that allow a portion of a fluid sample that has been introduced onto a diagnostic consumable to be flowed into a secondary sensing region could be used in any of a variety of applications where fluid sample analysis via multiple analyses in multiple sensing regions on a diagnostic consumable would be advantageous. For example, a single-use diagnostic consumable in accordance with the present disclosure may include a fluid transport material configured for use as a lateral flow immunoassay to confirm the presence or absence of a target analyte in a fluid sample, such as pathogens or biomarkers in humans or animals, or contaminants in water supplies, foodstuffs, or animal feeds. In accordance with the present disclosure, such diagnostic consumables also include at least one sensing region that includes one or more sensors configured to provide an additional analysis of the fluid sample, such as electrochemical sensors for measuring the concentration of gases, electrolytes and/or metabolites in human or animal bodily fluids, or other contaminants in water supplies, foodstuffs, or animal feeds.

ILLUSTRATIVE EMBODIMENTS

The following provides a non-limiting list of additional Illustrative Embodiments of the present disclosure:

Example Embodiment 1. A single-use diagnostic consumable for use in the analysis of whole blood and plasma, the diagnostic consumable comprising:

a first sensing region configured for analysis of at least one analyte in a whole blood sample that has been received by the diagnostic consumable;

a plasma separation membrane configured to separate plasma and blood cells in the whole blood sample to produce a plasma sample; and a second sensing region fluidically connected to the plasma separation membrane and configured for analysis of the plasma sample.

Example Embodiment 2. The single-use diagnostic consumable of Example Embodiment 1, wherein the second sensing region is adjacent to one end of the plasma separation membrane.

Example Embodiment 3. The single-use diagnostic consumable of Example Embodiment 2, wherein the plasma separation membrane defines a path for capillary fluid flow through the plasma separation membrane to the second sensing region.

Example Embodiment 4. The single-use diagnostic consumable of any of Example Embodiments 1 to 3, wherein at least a portion of the second sensing region is optically transparent to permit an optical assay of the plasma sample.

Example Embodiment 5. The single-use diagnostic consumable of Example Embodiment 4, wherein the second sensing region is configured for colorimetric analysis of the plasma sample.

Example Embodiment 6. The single-use diagnostic consumable of any of Example Embodiments 1 to 5, wherein the plasma separation membrane comprises a chromatographic detection pad for detecting a presence of free hemoglobin in the whole blood sample.

Example Embodiment 7. The single-use diagnostic consumable of any of Example Embodiments 1 to 6, wherein the plasma separation membrane comprises at least one component configured to selectively bind to an analyte of interest in the whole blood sample.

Example Embodiment 8. The single-use diagnostic consumable of Example Embodiment 7, wherein the at least one component configured to selectively bind to an analyte of interest in the whole blood sample comprises a least one type of red blood cell binding or agglutination material.

Example Embodiment 9. The single-use diagnostic consumable of any of Example Embodiments 1 to 8, wherein the first sensing region comprises a sensor array for analysis of multiple analytes in the whole blood sample.

Example Embodiment 10. The single-use diagnostic consumable of any of Example Embodiments 1 to 9, wherein the diagnostic consumable further comprises a sample input port for receiving the whole blood sample, the sample input port being fluidically connected to the first sensing region and the plasma separation membrane.

Example Embodiment 11. The single-use diagnostic consumable of Example Embodiment 10, wherein the plasma separation membrane is fluidically connected downstream of the first sensing region relative to the sample input port.

Example Embodiment 12. The single-use diagnostic consumable of Example Embodiment 10, wherein the plasma separation membrane is fluidically connected upstream of the first sensing region relative to the sample input port.

Example Embodiment 13. The single-use diagnostic consumable of Example Embodiment 10, wherein the plasma separation membrane substantially surrounds the sample input port.

Example Embodiment 14. The single-use diagnostic consumable of Example Embodiment 10, wherein the plasma separation membrane has a first end and a second end, the first end being adjacent to the sample input port and the second end being adjacent to the second sensing region.

Example Embodiment 15. The single-use diagnostic consumable of any of Example Embodiments 10 to 14, wherein the diagnostic consumable further comprises one or more sample distribution channels fluidically connected to the sample input port, the first sensing region and the plasma separation membrane.

Example Embodiment 16. The single-use diagnostic consumable of Example Embodiment 15, wherein the one or more sample distribution channels direct a first portion of the whole blood sample to the first sensing region for analysis of the whole blood sample, and direct a second portion of the whole blood sample into fluidic contact with the plasma separation membrane to produce the plasma sample.

Example Embodiment 17. The single-use diagnostic consumable of any of Example Embodiments 10 to 16, further comprising a third sensing region, fluidically connected to the sample input port, and configured for analysis of at least one analyte in the whole blood sample, the analysis in the third sensing region differing from the analysis in the first sensing region.

Example Embodiment 18. The single-use diagnostic consumable of Example Embodiment 17, wherein the third sensing region comprises:

a hemolysis channel fluidically connected to the sample input port, the hemolysis channel having disposed thereon a hemolytic reagent for hemolyzing a portion of the whole blood sample to generate a hemolyzed blood sample; and a chamber, fluidically connected to the hemolysis channel, and configured for containing at least a portion of the hemolyzed blood sample for analysis.

Example Embodiment 19. The single-use diagnostic consumable of Example Embodiment 18, wherein at least a portion of the chamber is optically transparent to permit an optical assay of the hemolyzed blood sample.

Example Embodiment 20. A method for analysis of whole blood and plasma on a single-use diagnostic consumable, the method comprising:

receiving a whole blood sample on the single-use diagnostic consumable;

analyzing at least one analyte in the whole blood sample in a first sensing region of the diagnostic consumable;

separating plasma and blood cells in the whole blood sample on the diagnostic consumable using a plasma separation membrane to produce a plasma sample; and optically analyzing the plasma sample in a second sensing region of the diagnostic consumable, at least a portion of the second sensing region being optically transparent to permit an optical assay of the plasma sample.

Example Embodiment 21. The method of Example Embodiment 20, wherein optically analyzing the plasma sample in the second sensing region comprises performing a colorimetric analysis of the plasma sample.

Example Embodiment 22. The method of Example Embodiment 21, wherein performing a colorimetric analysis of the plasma sample comprises:

measuring an amount of red light that is reflected by the plasma sample in the second sensing region; and determining a level of free hemoglobin in the whole blood sample based on the measured amount of reflected red light.

Example Embodiment 23. The method of Example Embodiment 20, wherein the plasma separation membrane comprises at least one component configured to selectively bind to an analyte of interest in the whole blood sample, and wherein optically analyzing the plasma sample in the second sensing region comprises optically detecting whether a bound analyte of interest is present in the plasma sample.

Example Embodiment 24. The method of any of Example Embodiments 20 to 23, wherein analyzing at least one analyte in the whole blood sample in the first sensing region comprises analyzing multiple analytes in the whole blood sample using a sensor array in the first sensing region.

Example Embodiment 25. The method of any of Example Embodiments 20 to 24, wherein the diagnostic consumable comprises a sample input port for receiving the whole blood sample, the method further comprising:

directing a first portion of the whole blood sample from the sample input port to the first sensing region for analysis of the whole blood sample; and directing a second portion of the whole blood sample from the sample input port into fluidic contact with the plasma separation membrane to produce the plasma sample.

Example Embodiment 26. The method of any of Example Embodiments 20 to 25, further comprising:

hemolyzing a portion of the whole blood sample on the diagnostic consumable to generate a hemolyzed blood sample; and optically analyzing the hemolyzed blood sample in a third sensing region on the diagnostic consumable, at least a portion of the third sensing region being optically transparent to permit an optical assay of the hemolyzed blood sample.

The inventive concepts disclosed herein are not limited in their application to the details of construction and the arrangement of the components set forth in the description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

Numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

The invention claimed is:

1. A single-use diagnostic consumable for use in the analysis of a fluid sample, the diagnostic consumable comprising:

a substrate having a top surface, a bottom surface, and a thickness therebetween, the substrate including:

a first sensing region that includes at least one sensor configured for a first analysis of a fluid sample that has been received by the diagnostic consumable;

a second sensing region configured for a second analysis of the fluid sample;

a fluid transport material configured to flow a portion of the fluid sample into the second sensing region; and a sample input port for receiving the fluid sample, the sample input port fluidically connected to the fluid transport material; wherein:

the first sensing region or the second sensing region extends through the thickness of the substrate and is open at the top surface and the bottom surface of the substrate; and the fluid transport material or the second sensing region comprises a reagent that reacts with an analyte of interest in the fluid sample.

2. The single-use diagnostic consumable of claim 1, wherein the second sensing region is adjacent to one end of the fluid transport material.

3. The single-use diagnostic consumable of claim 2, wherein the fluid transport material defines a path for capillary fluid flow through the fluid transport material to the second sensing region.

4. The single-use diagnostic consumable of claim 1, wherein at least a portion of the second sensing region is optically transparent to permit an optical assay of the portion of the fluid sample within the second sensing region.

5. The single-use diagnostic consumable of claim 4, wherein the second sensing region is configured for colorimetric analysis.

6. The single-use diagnostic consumable of claim 1, wherein the fluid transport material comprises at least one component configured to selectively bind to an analyte of interest in the fluid sample.

7. The single-use diagnostic consumable of claim 6, wherein the fluid sample comprises a whole blood sample, and wherein the at least one component configured to selectively bind to an analyte of interest in the fluid sample comprises a least one type of red blood cell binding or agglutination material.

8. The single-use diagnostic consumable of claim 1, wherein the fluid sample comprises a bodily fluid sample.

9. The single-use diagnostic consumable of claim 8, wherein the bodily fluid is blood or urine.

10. The single-use diagnostic consumable of claim 8, wherein the bodily fluid sample comprises a whole blood sample, and wherein the fluid transport material comprises a plasma separation membrane configured to separate plasma and blood cells in the whole blood sample to produce a plasma sample for analysis in the second sensing region.

11. The single-use diagnostic consumable of claim 1, wherein the fluid sample comprises a whole blood sample, and wherein the fluid transport material comprises a chromatographic detection pad for detecting a presence of free hemoglobin in the whole blood sample.

12. The single-use diagnostic consumable of claim 1, wherein the first sensing region comprises a sensor array for analysis of multiple analytes in the fluid sample.

13. The single-use diagnostic consumable of claim 12, wherein the sensor array comprises electrochemical sensors configured for measuring concentrations of gases, electrolytes and/or metabolites in the fluid sample.

14. The single-use diagnostic consumable of claim 13, wherein the fluid sample comprises a whole blood sample.

15. The single-use diagnostic consumable of claim 1, wherein the sample input port is also fluidically connected to the first sensing region.

16. The single-use diagnostic consumable of claim 15, wherein the fluid transport material is fluidically connected downstream of the first sensing region relative to the sample input port.

17. The single-use diagnostic consumable of claim 15, wherein the fluid transport material is fluidically connected upstream of the first sensing region relative to the sample input port.

18. The single-use diagnostic consumable of claim 15, wherein the fluid transport material has a first end and a second end, the first end adjacent to the sample input port and the second end adjacent to the second sensing region.

19. The single-use diagnostic consumable of claim 15, wherein the diagnostic consumable further comprises one or more sample distribution channels fluidically connected to the sample input port, the first sensing region and the fluid transport material.

20. The single-use diagnostic consumable of claim 19, wherein the one or more sample distribution channels direct a first portion of the fluid sample to the first sensing region for analysis of the fluid sample, and direct a second portion of the fluid sample into fluidic contact with the fluid transport material.

21. The single-use diagnostic consumable of claim 15, further comprising a third sensing region, fluidically connected to the sample input port, and configured for analysis of at least one analyte in the fluid sample, the analysis in the third sensing region differing from the analysis in the first sensing region.

22. The single-use diagnostic consumable of claim 21, wherein the third sensing region comprises:

a channel fluidically connected to the sample input port, the channel having disposed thereon a material for mixing with the fluid sample to generate a prepared fluid sample for analysis in the third sensing region; and a chamber, fluidically connected to the channel, and configured for containing at least a portion of the prepared fluid sample for analysis.

23. The single-use diagnostic consumable of claim 22, wherein at least a portion of the chamber is optically transparent to permit an optical assay of the prepared fluid sample.

24. The single-use diagnostic consumable of claim 22, wherein:

the fluid sample comprises a whole blood sample; and the channel fluidically connected to the sample input port comprises a hemolysis channel having disposed thereon a haemolytic reagent for hemolyzing a portion of the fluid sample to generate a hemolyzed blood sample.

25. A single-use diagnostic consumable for use in the analysis of a fluid sample, the diagnostic consumable comprising:

a first sensing region that includes at least one sensor configured for a first analysis of a fluid sample that has been received by the diagnostic consumable;

a second sensing region configured for a second analysis of the fluid sample;

a fluid transport material configured to flow a portion of the fluid sample into the second sensing region; and a sample input port for receiving the fluid sample, the sample input port fluidically connected to the fluid transport material; wherein:

the fluid transport material substantially surrounds the sample input port; and the fluid transport material comprises a plasma separation membrane configured to separate plasma and blood cells in a whole blood sample to produce a plasma sample for analysis in the second sensing region.

\* \* \* \* \*